United States Patent
Hatanaka et al.

[11] Patent Number: 6,127,339
[45] Date of Patent: Oct. 3, 2000

[54] PEPTIDE FOR BINDING THERETO A LOW DENSITY LIPOPROTEIN

[75] Inventors: Yoshihiro Hatanaka, Fuji; Masaharu Aritomi, Kawanishi, both of Japan

[73] Assignees: Asahi Kasei Kogyo Kabushiki Kaisha, Osaka; Asahi Medical Co., Ltd., Tokyo, both of Japan

[21] Appl. No.: 08/981,122

[22] PCT Filed: Jun. 21, 1996

[86] PCT No.: PCT/JP96/01734

§ 371 Date: Dec. 18, 1997

§ 102(e) Date: Dec. 18, 1997

[87] PCT Pub. No.: WO97/00889

PCT Pub. Date: Jan. 9, 1997

[30] Foreign Application Priority Data

Jun. 21, 1995 [JP] Japan ................................ 7-176904

[51] Int. Cl.[7] .................................................. A61K 38/00
[52] U.S. Cl. ........................ 514/15; 514/16; 514/17; 514/18; 514/19; 514/824; 530/328; 530/329; 530/330; 530/331; 530/812; 530/814; 530/815
[58] Field of Search ........................ 530/328, 329, 530/330, 331, 812, 814, 815; 514/15–19, 824

[56] References Cited

U.S. PATENT DOCUMENTS 5,464,820  11/1995  Burton et al. ............................. 514/16

FOREIGN PATENT DOCUMENTS

| 0 110 409 | 6/1984 | European Pat. Off. . |
| 0 225 867 | 6/1987 | European Pat. Off. . |
| 0 561 379 | 9/1993 | European Pat. Off. . |
| 62-56782 | 11/1987 | Japan . |
| 63-19214 | 4/1988 | Japan . |
| 6-157591 | 3/1994 | Japan . |
| WO 90/04416 | 5/1990 | WIPO . |
| 9602267 | 1/1996 | WIPO . |

OTHER PUBLICATIONS

O. Wiklund et al., "Cationic Polypeptides In Vitro Association of Low Density Lipoprotein with Arterial Proteoglycans, Fibroblasts, and Arterial Tissue", Sep./Oct. 1990, pp. 695–702, *Arteriosclerosis*, vol. 10, No. 5.

U. Olsson et al., "Binding of a Synthetic Apolipoprotein B–100 Peptide and Peptide Analogues to Chondroitin 6–Sulfate: Effects of the Lipid Environment", 1993, pp. 1858–1865, *Biochemistry*, vol. 32, No. 7.

CAPLUS DN 107:192315, Protter et al., WO 8702061 A1, Apr. 9, 1987.

HCAPLUS AN: 1995: 846295, Daniels et al., *Mol. Pharmacol.*, 48(3), pp. 425–432. (abstract), 1995.

HCAPLUS AN: 1994: 672404, Hlavacek et al., Pept. 1992, Proc. Eur. Pept. Symp., $22^{nd}$, 741–2, 1993.

Rudinger, *Peptide Homones*, Jun. 1976, pp. 1–7.

*Primary Examiner*—Dwayne C. Jones
*Assistant Examiner*—C. Delacroix-Muirheid
*Attorney, Agent, or Firm*—Young & Thompson

[57] ABSTRACT

Disclosed is a peptide for binding thereto a low density lipoprotein, which has an amino acid sequence represented by the formula (I) or (II) and which has an electric charge (E) satisfying the following requirement: $+1 \leq E \leq +4$ wherein E is defined by the formula: E=(the number of positive functional groups present in the peptide)–(the number of negative functional groups present in the peptide):

$$(X^1)_p\text{-}(\alpha)_m\text{-}(X^2)_q\text{-}(\beta)_n\text{-}(X^3)_r, \text{ or} \quad \text{(I)}$$

$$(X^1)_p\text{-}(\beta)_n\text{-}(X^2)_q\text{-}(\alpha)_m\text{-}(X^3)_r \quad \text{(II)}$$

wherein each a is independently Phe or Trp; each p is independently Arg or Lys; each $X^1$, each $X^2$ and each $X^3$ are individually, independently an arbitrary amino acid residue; and m, n, p, q and r satisfy the following requirement: $2 \leq m+n+p+q+r \leq 10$, wherein m and n satisfy the following requirements: $2 \leq m+n \leq 10$ and $1 \leq m$, $n \leq 9$, and p, q and r satisfy the following requirements: $0 \leq p+q+r \leq 8$, $0 \leq p$, $r \leq 8$ and $0 \leq q \leq 5$. The peptide of the present invention is advantageous in that the peptide not only has an excellent ability to specifically bind thereto an LDL, but also is excellent in safety, so that it can be advantageously used not only as a reagent for adsorption-removing an LDL from a body fluid, but also as a peptide drug or a carrier peptide for a drug for treating a disease caused by an LDL.

4 Claims, 1 Drawing Sheet

```
                            SEQUENCE LISTING

<160> NUMBER OF SEQ ID NOS: 90

<210> SEQ ID NO 1
<211> LENGTH: 5
<212> TYPE: PRT
<213> ORGANISM: Artificial Sequence
<220> FEATURE:
<223> OTHER INFORMATION: Sequence of a peptide synthesized in Example
      1 from L-form F-moc amino acids by solid phase method using a
      multipeptide synthesizing system (RaMPS; manufactured and sold by
      NEN Research Products, U.S.A.)

<400> SEQUENCE: 1

Arg Phe Tyr Tyr Met
 1               5

<210> SEQ ID NO 2
<211> LENGTH: 5
<212> TYPE: PRT
<213> ORGANISM: Artificial Sequence
<220> FEATURE:
<223> OTHER INFORMATION: Sequence of a peptide synthesized in Example
      1 from L-form F-moc amino acids by solid phase method using a
      multipeptide synthesizing system (RaMPS)

<400> SEQUENCE: 2

Phe Lys Ile Trp Trp
 1               5

<210> SEQ ID NO 3
<211> LENGTH: 5
<212> TYPE: PRT
<213> ORGANISM: Artificial Sequence
<220> FEATURE:
<223> OTHER INFORMATION: Sequence of a peptide synthesized in Example
      1 from L-form F-moc amino acids by solid phase method using a
      multipeptide synthesizing system (RaMPS)

<400> SEQUENCE: 3

Trp Gln Arg His Phe
 1               5

<210> SEQ ID NO 4
<211> LENGTH: 5
<212> TYPE: PRT
<213> ORGANISM: Artificial Sequence
<220> FEATURE:
<223> OTHER INFORMATION: Sequence of a peptide synthesized in Example
      1 from L-form F-moc amino acids by solid phase method using a
      multipeptide synthesizing system (RaMPS)

<400> SEQUENCE: 4

Ile Phe Tyr Lys Trp
 1               5

<210> SEQ ID NO 5
<211> LENGTH: 5
<212> TYPE: PRT
```

```
<213> ORGANISM: Artificial Sequence
<220> FEATURE:
<223> OTHER INFORMATION: Sequence of a peptide synthesized in Example
      1 from L-form F-moc amino acids by solid phase method using a
      multipeptide synthesizing system (RaMPS)

<400> SEQUENCE: 5

Trp Ala Leu Tyr Arg
 1               5

<210> SEQ ID NO 6
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 6

Trp Thr Ala Arg Arg
 1               5

<210> SEQ ID NO 7
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 7

Phe Ala Tyr Arg Arg
 1               5

<210> SEQ ID NO 8
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 8

Arg Trp Ile Leu Gln
 1               5

<210> SEQ ID NO 9
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 9

Arg Phe Trp Leu Phe
 1               5

<210> SEQ ID NO 10
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
``` multipeptide synthesizing system (RaMPS)

<400> SEQUENCE: 10

Arg Tyr Ala Phe Trp
 1               5

<210> SEQ ID NO 11
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 11

Lys His Ile Tyr Trp
 1               5

<210> SEQ ID NO 12
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 12

Trp Arg Tyr Asp Arg
 1               5

<210> SEQ ID NO 13
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 13

Leu Lys Trp Phe Gln
 1               5

<210> SEQ ID NO 14
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 14

Tyr Tyr Arg Trp Phe
 1               5

<210> SEQ ID NO 15
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 15

```
Leu Trp Lys Ser Phe
  1               5

<210> SEQ ID NO 16
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 16

Phe Phe Trp Arg Gly
  1               5

<210> SEQ ID NO 17
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 17

Leu Asn Phe Arg Trp
  1               5

<210> SEQ ID NO 18
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 18

Phe Leu Met Arg Phe
  1               5

<210> SEQ ID NO 19
<211> LENGTH: 5
<212> TYPE: PRT
<213> ORGANISM: Artificial Sequence
<220> FEATURE:
<223> OTHER INFORMATION: Sequence of a peptide synthesized in Example
      2 from L-form F-moc amino acids by solid phase method using a
      multipeptide synthesizing system (RaMPS)

<400> SEQUENCE: 19

Trp Leu Met Trp Arg
  1               5

<210> SEQ ID NO 20
<211> LENGTH: 5
<212> TYPE: PRT
<213> ORGANISM: Artificial Sequence
<220> FEATURE:
<223> OTHER INFORMATION: Sequence of a peptide synthesized in Example
      3 from L-form F-moc amino acids by solid phase method using a
      multipeptide synthesizing system (RaMPS)

<400> SEQUENCE: 20

Trp Ala Trp Arg Arg
  1               5
```

<210> SEQ ID NO 21
<211> LENGTH: 5
<212> TYPE: PRT
<213> ORGANISM: Artificial Sequence
<220> FEATURE:
<223> OTHER INFORMATION: Sequence of a peptide synthesized in Example
      3 from L-form F-moc amino acids by solid phase method using a
      multipeptide synthesizing system (RaMPS)

<400> SEQUENCE: 21

Leu Phe Leu Met Arg
 1               5

<210> SEQ ID NO 22
<211> LENGTH: 10
<212> TYPE: PRT
<213> ORGANISM: Artificial Sequence
<220> FEATURE:
<223> OTHER INFORMATION: Sequence of a peptide synthesized in Example
      3 from L-form F-moc amino acids by solid phase method using a
      multipeptide synthesizing system (RaMPS)

<400> SEQUENCE: 22

Trp Ala Trp Arg Arg Gly Gly Gly Gly Gly
 1               5                  10

<210> SEQ ID NO 23
<211> LENGTH: 10
<212> TYPE: PRT
<213> ORGANISM: Artificial Sequence <220>
<220> FEATURE:
<223> OTHER INFORMATION: Sequence of a peptide synthesized in Example
      3 from L-form F-moc amino acids by solid phase method using a
      multipeptide synthesizing system (RaMPS)

<400> SEQUENCE: 23

Leu Phe Leu Met Arg Gly Gly Gly Gly Gly
 1               5                  10

<210> SEQ ID NO 24
<211> LENGTH: 4
<212> TYPE: PRT
<213> ORGANISM: Artificial Sequence
<220> FEATURE:
<223> OTHER INFORMATION: Sequence of a peptide synthesized in Example
      4 from L-form F-moc amino acids by solid phase method using a
      multipeptide synthesizing system (RaMPS)

<400> SEQUENCE: 24

Trp Phe Trp Arg
 1

<210> SEQ ID NO 25
<211> LENGTH: 4
<212> TYPE: PRT
<213> ORGANISM: Artificial Sequence
<220> FEATURE:
<223> OTHER INFORMATION: Sequence of a peptide synthesized in Example
      4 from L-form F-moc amino acids by solid phase method using a
      multipeptide synthesizing system (RaMPS)

<400> SEQUENCE: 25

Trp Phe Trp Lys
 1

<210> SEQ ID NO 26
<211> LENGTH: 5
<212> TYPE: PRT
<213> ORGANISM: Artificial Sequence

```
<220> FEATURE:
<223> OTHER INFORMATION: Sequence of peptides synthesized in Examples
      4 and 5 from L-form F-moc amino acids by solid phase method using
      a multipeptide synthesizing system (RaMPS) or an automatic peptide
      synthesizer (9050 plus peptide synthesizer: sold by Nihon
      PerSpeptive Ltd. Japan)

<400> SEQUENCE: 26

Trp Phe Trp Arg Arg
  1               5

<210> SEQ ID NO 27
<211> LENGTH: 5
<212> TYPE: PRT
<213> ORGANISM: Artificial Sequence
<220> FEATURE:
<223> OTHER INFORMATION: Sequence of a peptide synthesized in Example
      4 from L-form F-moc amino acids by solid phase method using a
      multipeptide synthesizing system (RaMPS).

<400> SEQUENCE: 27

Trp Phe Trp Lys Lys
  1               5

<210> SEQ ID NO 28
<211> LENGTH: 4
<212> TYPE: PRT
<213> ORGANISM: Artificial Sequence
<220> FEATURE:
<223> OTHER INFORMATION: Sequence of a peptide synthesized in Example
      5 from L-form F-moc amino acids by solid phase method using a
      multipeptide synthesizing system (RaMPS)

<400> SEQUENCE: 28

Trp Trp Trp Arg
  1

<210> SEQ ID NO 29
<211> LENGTH: 4
<212> TYPE: PRT
<213> ORGANISM: Artificial Sequence
<220> FEATURE:
<223> OTHER INFORMATION: Sequence of a peptide synthesized in Example
      6 from L-form F-moc amino acids by solid phase method using a
      multipeptide synthesizing system (RaMPS)

<400> SEQUENCE: 29

Trp Ala Ala Arg
  1

<210> SEQ ID NO 30
<211> LENGTH: 5
<212> TYPE: PRT
<213> ORGANISM: Artificial Sequence
<220> FEATURE:
<223> OTHER INFORMATION: Sequence of a peptide synthesized in Example
      6 from L-form F-moc amino acids by solid phase method using a
      multipeptide synthesizing system (RaMPS)

<400> SEQUENCE: 30

Trp Ala Ala Ala Arg
  1               5

<210> SEQ ID NO 31
<211> LENGTH: 6
<212> TYPE: PRT
<213> ORGANISM: Artificial Sequence
<220> FEATURE:
<223> OTHER INFORMATION: Sequence of a peptide synthesized in Example
```

6 from L-form F-moc amino acids by solid phase method using a
      multipeptide synthesizing system (RaMPS)

<400> SEQUENCE: 31

Trp Ala Ala Ala Ala Arg
 1               5

<210> SEQ ID NO 32
<211> LENGTH: 7
<212> TYPE: PRT
<213> ORGANISM: Artificial Sequence
<220> FEATURE:
<223> OTHER INFORMATION: Sequence of a peptide synthesized in Example
      6 from L-form F-moc amino acids by solid phase method using a
      multipeptide synthesizing system (RaMPS)

<400> SEQUENCE: 32

Trp Ala Ala Ala Ala Ala Arg
 1               5

<210> SEQ ID NO 33
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      7 to 11 from L-form F-moc amino acids by solid phase method using
      an automatic peptide synthesizer (9050 plus peptide synthesizer)

<400> SEQUENCE: 33

Trp Phe Trp Arg Lys
 1               5

<210> SEQ ID NO 34
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      7 to 12 from L-form F-moc amino acids by solid phase method using
      an automatic peptide synthesizer (9050 plus peptide synthesizer)

<400> SEQUENCE: 34

Lys Arg Trp Phe Trp
 1               5

<210> SEQ ID NO 35
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      1 to 13 from L-form F-moc amino acids by solid phase method using
      an automatic peptide synthesizer (9050 plus peptide synthesizer)

<400> SEQUENCE: 35

Arg Arg Trp Phe Trp
 1               5

<210> SEQ ID NO 36

```
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 36

Trp Leu Phe Phe Arg
 1               5

<210> SEQ ID NO 37
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 37

Phe Phe Phe Arg Trp
 1               5

<210> SEQ ID NO 38
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of a peptide synthesized in Examples
      11 and 12 from L-form F-moc amino acids by solid phase method
      using an automatic peptide synthesizer (9050 plus peptide
      synthesizer)

<400> SEQUENCE: 38

Arg Phe Phe Leu Trp
 1               5

<210> SEQ ID NO 39
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 39

Arg Arg Trp Phe Phe
 1               5

<210> SEQ ID NO 40
<211> LENGTH: 5
<212> TYPE: PRT
<213> ORGANISM: Artificial Sequence
```

```
<220> FEATURE:
<221> NAME/KEY: AMIDATION
<222> LOCATION: 5
<220> FEATURE:
<223> OTHER INFORMATION: Sequence of peptides synthesized in Examples
      11 to 13 from L-form F-moc amino acids by solid phase method using
      an automatic peptide synthesizer (9050 plus peptide synthesizer)

<400> SEQUENCE: 40

Arg Arg Trp Ala Trp
 1               5

<210> SEQ ID NO 41
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of a peptide synthesized in Example
      11 from L-form F-moc amino acids by solid phase method using an
      automatic peptide synthesizer (9050 plus peptide synthesizer)

<400> SEQUENCE: 41

Arg Lys Val Trp Trp
 1               5

<210> SEQ ID NO 42
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 42

Lys Arg Val Trp Trp
 1               5

<210> SEQ ID NO 43
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 43

Lys Phe Phe Leu Trp
 1               5

<210> SEQ ID NO 44
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of a peptide synthesized in Example
```

11 from L-form F-moc amino acids by solid phase method using an
automatic peptide synthesizer (9050 plus peptide synthesizer)

<400> SEQUENCE: 44

Lys Met Leu Phe Phe
 1               5

<210> SEQ ID NO 45
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 45

Lys Trp Leu Phe Trp
 1               5

<210> SEQ ID NO 46
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 46

Arg Arg Trp Trp Trp
 1               5

<210> SEQ ID NO 47
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 47

Arg Arg Trp Trp Phe
 1               5

<210> SEQ ID NO 48
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

```
<400> SEQUENCE: 48

Arg Arg Phe Trp Trp
 1               5

<210> SEQ ID NO 49
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 49

Arg Arg Phe Phe Trp
 1               5

<210> SEQ ID NO 50
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 50

Arg Arg Phe Trp Phe
 1               5

<210> SEQ ID NO 51
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 51

Arg Arg Trp Leu Trp
 1               5

<210> SEQ ID NO 52
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 52

Arg Arg Trp Val Trp
```

1          5

<210> SEQ ID NO 53
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 53

Arg Arg Trp Ile Trp
 1               5

<210> SEQ ID NO 54
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 54

Arg Arg Trp Tyr Trp
 1               5

<210> SEQ ID NO 55
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 55

Arg Arg Trp Ser Trp
 1               5

<210> SEQ ID NO 56
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 to 13 from L-form F-moc amino acids by solid phase method using
      an automatic peptide synthesizer (9050 plus peptide synthesizer)

<400> SEQUENCE: 56

Arg Arg Trp Arg Trp
 1               5

<210> SEQ ID NO 57

```
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 to 13 from L-form F-moc amino acids by solid phase method using
      an automatic peptide synthesizer (9050 plus peptide synthesizer)

<400> SEQUENCE: 57

Arg Arg Trp Glu Trp
 1               5

<210> SEQ ID NO 58
<211> LENGTH: 4
<212> TYPE: PRT
<213> ORGANISM: Artificial Sequence
<220> FEATURE:
<221> NAME/KEY: AMIDATION
<222> LOCATION: 4
<220> FEATURE:
<223> OTHER INFORMATION: Sequence of a peptide synthesized in Example
      12 from L-form F-moc amino acids by solid phase method using an
      automatic peptide synthesizer (9050 plus peptide synthesizer)

<400> SEQUENCE: 58

Arg Phe Phe Trp
 1

<210> SEQ ID NO 59
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of a peptide synthesized in Example
      12 from L-form F-moc amino acids by solid phase method using an
      automatic peptide synthesizer (9050 plus peptide synthesizer)

<400> SEQUENCE: 59

Arg Arg Phe Phe Phe
 1               5

<210> SEQ ID NO 60
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of a peptide synthesized in Example
      12 from L-form F-moc amino acids by solid phase method using an
      automatic peptide synthesizer (9050 plus peptide synthesizer)

<400> SEQUENCE: 60

Phe Phe Phe Arg Arg
 1               5

<210> SEQ ID NO 61
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
```

```
<223> OTHER INFORMATION: Sequence of a peptide synthesized in Example
      12 from L-form F-moc amino acids by solid phase method using an
      automatic peptide synthesizer (9050 plus peptide synthesizer)

<400> SEQUENCE: 61

Lys Arg Phe Phe Phe
 1               5

<210> SEQ ID NO 62
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 1 from L-form F-moc amino acids by solid phase
      method using a multipeptide synthesizing system (RaMPS)

<400> SEQUENCE: 62

Arg Ala His Ile Asn
 1               5

<210> SEQ ID NO 63
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 1 from L-form F-moc amino acids by solid phase
      method using a multipeptide synthesizing system (RaMPS)

<400> SEQUENCE: 63

Pro Lys Ser Ile Asn
 1               5

<210> SEQ ID NO 64
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 1 from L-form F-moc amino acids by solid phase
      method using a multipeptide synthesizing system (RaMPS)

<400> SEQUENCE: 64

Leu His Arg His Leu
 1               5

<210> SEQ ID NO 65
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 1 from L-form F-moc amino acids by solid phase
      method using a multipeptide synthesizing system (RaMPS)

<400> SEQUENCE: 65

Leu Thr Met Lys Met
 1               5

<210> SEQ ID NO 66
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 1 from L-form F-moc amino acids by solid phase
      method using a multipeptide synthesizing system (RaMPS)
```

-continued

<400> SEQUENCE: 66

Met Leu Thr Val Arg
 1               5

<210> SEQ ID NO 67
<211> LENGTH: 5
<212> TYPE: PRT
<213> ORGANISM: Artificial Sequence <220>
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 67

Thr His Arg Gln Arg
 1               5

<210> SEQ ID NO 68
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 68

His Tyr Tyr Leu Gln
 1               5

<210> SEQ ID NO 69
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 69

Trp His Val Gln Thr
 1               5

<210> SEQ ID NO 70
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 70

Pro Asn Ala Phe Ala
 1               5

<210> SEQ ID NO 71
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 71

His Trp Val Val His
 1               5

<210> SEQ ID NO 72
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 72

Tyr Ile Gln Val Trp
 1               5

<210> SEQ ID NO 73
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 73

Phe Gly Ala Ile Val
 1               5

<210> SEQ ID NO 74
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 74

His Ala Ser Asn Pro
 1               5

<210> SEQ ID NO 75
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 75

Glu Trp Ser Met Thr
 1               5

<210> SEQ ID NO 76
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 76

Phe Ile Ile Met Glu
 1               5

<210> SEQ ID NO 77
<211> LENGTH: 5

```
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 77

Trp Val Asp His Asn
 1               5

<210> SEQ ID NO 78
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 78

Glu Ala Lys His Glu
 1               5

<210> SEQ ID NO 79
<211> LENGTH: 5
<212> TYPE: PRT
<213> ORGANISM: Artificial Sequence
<220> FEATURE:
<223> OTHER INFORMATION: Sequence of a peptide synthesized in
      Comparative Example 2 from L-form F-moc amino acids by solid phase
      method using a multipeptide synthesizing system (RaMPS)

<400> SEQUENCE: 79

Phe Asn Phe Glu Ser
 1               5

<210> SEQ ID NO 80
<211> LENGTH: 5
<212> TYPE: PRT
<213> ORGANISM: Artificial Sequence
<220> FEATURE:
<223> OTHER INFORMATION: Sequence of peptides synthesized in
      Comparative Example 2 from L-form F-moc amino acids by solid phase
      method using a multipeptide synthesizing system (RaMPS) or an
      automatic peptide synthesizer (9050 plus peptide synthesizer)

<400> SEQUENCE: 80

Val Glu Glu Met Glu
 1               5

<210> SEQ ID NO 81
<211> LENGTH: 10
<212> TYPE: PRT
<213> ORGANISM: Artificial Sequence
<220> FEATURE:
<223> OTHER INFORMATION: Sequence of a peptide synthesized in
      Comparative Example 3 from L-form F-moc amino acids by solid phase
      method using a multipeptide synthesizing system (RaMPS)

<400> SEQUENCE: 81

Trp Ala Trp Glu Glu Gly Gly Gly Gly Gly
 1               5                  10

<210> SEQ ID NO 82
<211> LENGTH: 10
<212> TYPE: PRT
<213> ORGANISM: Artificial Sequence
<220> FEATURE:
```

```
<223> OTHER INFORMATION: Sequence of a peptide synthesized in
      Comparative Example 3 from L-form F-moc amino acids by solid phase
      method using a multipeptide synthesizing system (RaMPS)

<400> SEQUENCE: 82

Phe Phe Phe Phe Phe Gly Gly Gly Gly Gly
 1               5                   10

<210> SEQ ID NO 83
<211> LENGTH: 9
<212> TYPE: PRT
<213> ORGANISM: Artificial Sequence
<220> FEATURE:
<221> NAME/KEY: AMIDATION
<222> LOCATION: 10
<220> FEATURE:
<223> OTHER INFORMATION: Sequence of a peptide synthesized in
      Comparative Examples 4, 5 and 10 from L-form F-moc amino acids by
      solid phase method using an automatic peptide synthesizer (9050
      plus peptide synthesizer)

<400> SEQUENCE: 83

Gln Asp Gly Ser Asp Glu Val Tyr Lys
 1               5

<210> SEQ ID NO 84
<211> LENGTH: 9
<212> TYPE: PRT
<213> ORGANISM: Artificial Sequence
<220> FEATURE:
<221> NAME/KEY: AMIDATION
<222> LOCATION: 10
<220> FEATURE:
<223> OTHER INFORMATION: Sequence of a peptide synthesized in
      Comparative Example 4 from L-form F-moc amino acids by solid phase
      method using an automatic peptide synthesizer (9050 plus peptide
      synthesizer)

<400> SEQUENCE: 84

Gln Gly Asp Asp Ser Glu Val Tyr Lys
 1               5

<210> SEQ ID NO 85
<211> LENGTH: 15
<212> TYPE: PRT
<213> ORGANISM: Artificial Sequence
<220> FEATURE:
<223> OTHER INFORMATION: Sequence of a peptide synthesized in
      Comparative Example 7 from L-form F-moc amino acids by solid phase
      method using an automatic peptide synthesizer (9050 plus peptide
      synthesizer)
<300> PUBLICATION INFORMATION:
<301> AUTHORS: Urban Olsson et al.
<302> TITLE: Binding of a synthestic apolipoprotein B-100 peptide and
      peptide analogues to chondroitin 6-sulfate: Effects of the lipid
      environment
<303> JOURNAL: Biochemistry
<304> VOLUME: 32
<306> PAGES: 1858-1865

<400> SEQUENCE: 85

Val Val Trp Arg Leu Thr Arg Lys Arg Gly Leu Lys Val Val Val
 1               5                   10                  15

<210> SEQ ID NO 86
<211> LENGTH: 5
<212> TYPE: PRT
<213> ORGANISM: Artificial Sequence
<220> FEATURE:
<221> NAME/KEY: AMIDATION
<222> LOCATION: 5
```

```
<220> FEATURE:
<223> OTHER INFORMATION: Sequence of peptides synthesized in
      Comparative Examples 8 and 9 from L-form F-moc amino acids by
      solid phase method using an automatic peptide synthesizer (9050
      plus peptide synthesizer)

<400> SEQUENCE: 86

Asp Pro Ser Val Tyr
 1               5

<210> SEQ ID NO 87
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in
      Comparative Examples 8 and 9 from L-form F-moc amino acids by
      solid phase method using an automatic peptide synthesizer (9050
      plus peptide synthesizer)

<400> SEQUENCE: 87

Tyr Val Ser Pro Asp
 1               5

<210> SEQ ID NO 88
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in
      Comparative Examples 8 and 9 from L-form F-moc amino acids by
      solid phase method using an automatic peptide synthesizer (9050
      plus peptide synthesizer)

<400> SEQUENCE: 88

Glu Met Glu Glu Val
 1               5

<210> SEQ ID NO 89
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in Examples
      11 and 12 from L-form F-moc amino acids by solid phase method
      using an automatic peptide synthesizer (9050 plus peptide
      synthesizer)

<400> SEQUENCE: 89

Trp Phe Trp Arg Arg
 1               5

<210> SEQ ID NO 90
<211> LENGTH: 5
<212> TYPE: PRT
<213> ORGANISM: Artificial Sequence
<220> FEATURE:
<221> NAME/KEY: AMIDATION
<222> LOCATION: 5
<220> FEATURE:
<223> OTHER INFORMATION: Sequence of peptides synthesized in
      Comparative Examples 8 and 9 from L-form F-moc amino acids by
```

```
              -continued solid phase method using an automatic peptide synthesizer (9050
    plus peptide synthesizer)

<400> SEQUENCE: 90

Val Glu Glu Met Glu
 1               5
```

PEPTIDE FOR BINDING THERETO A LOW DENSITY LIPOPROTEIN

This application is a 371 of PCT/JP/960,734, filed Jun. 21, 1996.

BACKGROUND OF THE INVENTION

1. Field of the Invention

The present invention relate to a peptide for binding thereto a low density lipoprotein (hereinafter, frequently referred to simply as an "LDL") and an adsorbent comprising a water-insoluble carrier having bonded thereto the peptide. More particularly, the present invention is concerned with a peptide for binding thereto an LDL, wherein the peptide has a specific amino acid sequence comprising 2 to 10 amino acid residues including at least one Phe or Trp and at least one Arg or Lys and wherein the peptide has a specific electric charge (E) which is defined by the formula: E=(the number of positive functional groups present in the peptide)−(the number of negative functional groups present in the peptide). Further, the present invention is also concerned with an adsorbent for removing an LDL from a body fluid, comprising a water-insoluble carrier having bonded thereto the peptide. Still further, the present invention is also concerned with a method for removing an LDL from a body fluid, comprising contacting the body fluid with the peptide.

The peptide of the present invention is advantageous in that the peptide not only has an excellent ability to specifically bind thereto an LDL, but also is free from difficult problems, such as the production of a bradykinin, the activation of blood cells, the adsorption of blood cells onto the peptide and the activation of a blood coagulation system, thus leading to a safety in use of the peptide. Therefore, the peptide of the present invention can be advantageously used not only as a reagent for adsorption-removing an LDL from a body fluid, such as whole blood and plasma, but also as a peptide drug or a carrier peptide for a drug for treating a disease caused by an LDL. Further, the peptide of the present invention, which has the ability to bind thereto an LDL, has only 10 amino acid residues or less and, hence, is advantageous not only in that it can be easily prepared at low cost, but also in that it has excellent stability, such as sterilization stability and storage stability. Further, when an adsorbent comprising a water-insoluble carrier having bonded thereto the peptide of the present invention is employed in a blood purification treatment device or the like (which is necessarily used for removing the LDL from the blood of a patient suffering from a disease in which, due to a morbid factor, the LDL concentration of the blood is caused to increase to a level higher than that of the LDL concentration of the blood of a healthy person), the LDL can be efficiently, safely removed to advantage on the patient. In addition, when a soft gel (such as an agarose gel) or a hard gel (such as cross-linked polyvinyl alcohol) is used as the above-mentioned water-insoluble carrier in the adsorbent, the adsorbent can be advantageously used as a gel in liquid chromatography and the like for separating from an LDL-containing liquid the LDL in high purity form.

In the present specification, amino acid residues are represented using abbreviations, as indicated below, approved by IUPAC-IUB Commission on Biochemical Nomenclature (CBN). With respect to amino acids and the like having isomers, those which are represented by the following abbreviations are of either L-form or D-form. Further, the left and right ends of an amino acid sequence of a peptide are, respectively, the N- and C-termini unless otherwise specified.

A or Ala: alanine residue
D or Asp: aspartic acid residue
E or Glu: glutamic acid residue
F or Phe: phenylalanine residue
G or Gly: glycine residue
H or His: histidine residue
I or Ile: isoleucine residue
K or Lys: lysine residue
L or Leu: leucine residue
M or Met: methionine residue
N or Asn: asparagine residue
P or Pro: proline residue
Q or Gln: glutamine residue
R or Arg: arginine residue
S or Ser: serine residue
T or Thr: threonine residue
V or Val: valine residue
W or Trp: tryptophan residue
Y or Tyr: tyrosine residue
C or Cys: cysteine residue

2. Prior art

It has been known that, among the lipoproteins present in blood, an LDL contains a large amount of cholesterol and therefore is causative of arteriosclerosis. Conventionally, the treatment of a patient suffering from familial hypercholesterolemia, in which the LDL concentration of the blood of the patient is high, is conducted by extracorporeal blood circulation therapy (hereinafter, frequently referred to as an "LDL apheresis") using an adsorbent having the ability to adsorb an LDL, with the result that various symptoms of the patient have been ameliorated.

With respect to the known adsorbents for removing the LDL from blood, for example, European Patent No. 0 225 867 (corresponding to Examined Japanese Patent Application Publication Nos. 62-56782 and 63-19214) discloses a resin on which a polysaccharide sulfate having a negative charge is chemically immobilized as a ligand. As an example of such an adsorbent, there can be mentioned a cellulose particle carrier having dextran sulfate immobilized thereon as a ligand, which is commercially available.

However, when the LDL apheresis is conducted using such an LDL adsorbent having dextran sulfate as a ligand, a physiologically active substance called bradykinin is disadvantageously produced in the blood. The bradykinin is known to cause blood pressure depression, the contraction of a smooth muscle, the membrane-permeability sthenia and the like (see, for example, European Patent Application Publication No. 0 561 379 A1 (European Patent Application No. 93 104 348.3).

Further, WO90/04416 discloses an agarose particle on which the antibody having the ability to bind thereto a human low density lipoprotein is immobilized.

However, the use of an antibody in an LDL adsorbent has problems as follows. The antibody is generally produced in vitro or in vivo. Therefore, for preparing the antibody in an amount sufficient to treat a patient suffering from a disease caused by an LDL, large amounts of labor and cost are disadvantageously needed. Further, the antibody disadvantageously exhibits poor stability, especially in the sterilization thereof, so that the antibody cannot be safely used in an extracorporeal blood circulation therapy.

As further examples of substances suggested to have the ability to bind thereto an LDL, there can be mentioned a polylysine and a polyarginine, each having about 25 to 250 amino acid residues {see Olov Wiklund et al.; Cationic polypeptides modulate in vitro association of low density lipoprotein with arterial proteoglycans, fibloblasts, and arterial tissue. Arteriosclerosis. 10, 695–702 (1990)}; and a peptide having 15 amino acid residues of VVWRL-TRKRGLKVVV (see Urban Olsson et al.; Binding of a synthetic apolipoprotein B-100 peptide and peptide analogues to chondroitin 6-sulfate: Effects of the lipid environment. Biochemistry, 1993, 32, 1858–1865).

However, each of the above-mentioned polypeptides (i.e., the polylysine and the polyarginine, each having about 25 to 250 amino acid residues, and the polypeptide containing 15 amino acid resides of VVWRLTRKRGLKVVV) has more than 10 amino acid residues. Therefore, as in the case of the antibody, these polypeptides are poor with respect to stability, such as the sterilization stability and the storage stability.

On the other hand, with respect to a substance having a very high positive charge, it is known that when blood contacts with the surface of such a substance, disadvantages are caused such that the cell components of blood (such as erythrocytes, leukocytes and platelets) are activated and that the cell components are adsorbed on the surface of the above-mentioned substance due to a strong electrostatic interaction therebetween. Further, such a substance disadvantageously induces unfavorable phenomena, such as a non-specific adsorption of plasma proteins on the substance and the activation of a blood coagulation factor. Therefore, from the viewpoint of safety, it is not preferred to use the above-mentioned substance as an adsorbent in the LDL apheresis therapy.

Therefore, it has been desired to develop a new substance for binding thereto an LDL, which not only has an excellent ability to specifically bind thereto an LDL, but also does not cause disadvantages, such as the production of bradykinin, the activation of blood cells, the adsorption of blood cells on the substance and the activation of a blood coagulation system and which, therefore, can be advantageously used in an adsorbent for removing an LDL from a body fluid, such as whole blood or plasma.

SUMMARY OF THE INVENTION

In this situation, the present inventors have made extensive and intensive studies with a view toward solving the above-mentioned problems. As a result, it has unexpectedly been found that a peptide which has a specific amino acid sequence comprising 2 to 10 amino acid residues including at least one amino acid residue a (Phe or Trp) and at least one amino acid residue p (Arg or Lys) and which has an electric charge (E) satisfying the following requirement: $+1 \leq E \leq +4$ wherein E is defined by the formula: E=(the number of positive functional groups present in the peptide)−(the number of negative functional groups present in the peptide) can be advantageously used as an excellent substance for binding thereto a low density lipoprotein. That is, the peptide, on one hand, has an excellent ability to specifically bind thereto an LDL, and, on the other hand, is free from difficult problems, such as the production of a bradykinin, the activation of blood cells, the adsorption of blood cells on the peptide, the activation of a blood coagulation system and the like, thus leading to a safety in use of the peptide.

Further, since this peptide has only 10 amino acid residues or less, the peptide is advantageous not only in that it can be easily prepared at low cost, but also in that it has excellent stability during the operation for sterilization thereof, during the storage thereof, and the like.

Accordingly, it is an object of the present invention to provide a peptide for binding thereto an LDL, which not only has an excellent ability to specifically bind thereto an LDL, but also is free from difficult problems, such as the production of a bradykinin, the activation of blood cells, the adsorption of blood cells on the peptide, the activation of a blood coagulation system and the like, so that it can be safely, advantageously used not only as a reagent for adsorption-removing an LDL from a body fluid, such as whole blood and plasma, but also as a peptide drug or a carrier peptide for a drug for treating a disease caused by an LDL.

It is another object of the present invention to provide a peptide for binding thereto an LDL, which is advantageous not only in that it can be easily prepared at low cost, but also in that it exhibits excellent stability during the sterilization, the storage and the like.

It is still another object of the present invention to provide an adsorbent for removing an LDL from a body fluid, comprising a water-insoluble carrier having bonded thereto the peptide of the present invention, which is advantageous in that, when it is used in a blood purification treatment device or the like for LDL apheresis, the LDL can be efficiently, safely removed.

It is still another object of the present invention to provide a method for removing an LDL from a body fluid, comprising contacting the body fluid with the peptide of the present invention, whereby an efficient removal of an LDL form a body fluid can be safely achieved.

The foregoing and other objects, features and advantages of the present invention will be apparent from the following detailed description taken in connection with the accompanying drawing and the appended claims.

A BRIEF DESCRIPTION OF THE DRAWING

In the drawing:

FIG. 1. is a graph showing an example of profiles obtained by the measurement of the affinity of a peptide to an LDL using BIAcore (manufactured and sold by Pharmacia Biosensor AB, Sweden) as conducted in Example 12 and Comparative Example 9.

DETAILED DESCRIPTION OF THE INVENTION

Figure 1:
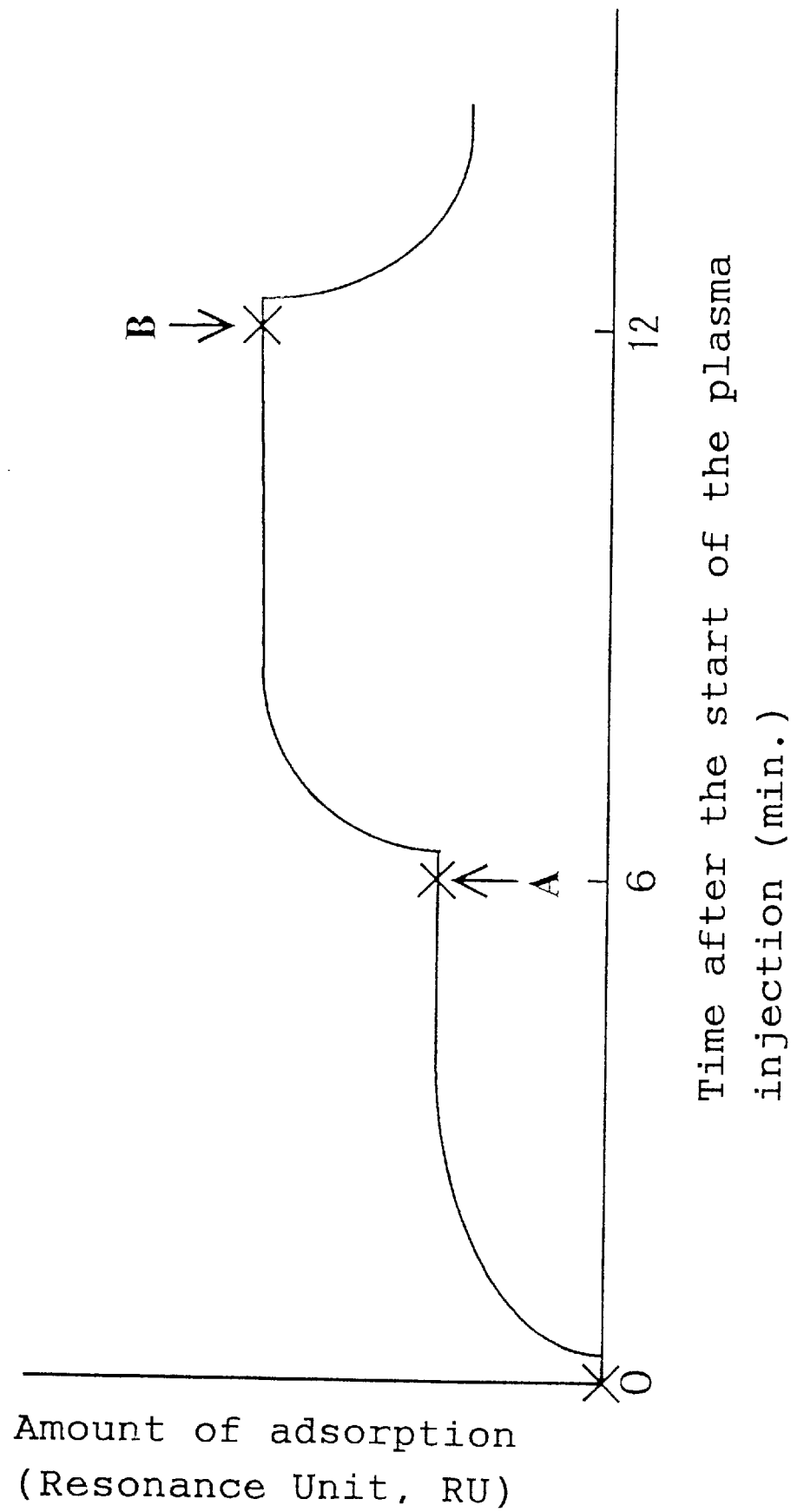

According to the present invention, there is provided a peptide for binding thereto a low density lipoprotein, having an amino acid sequence represented by the formula (I) or (II):

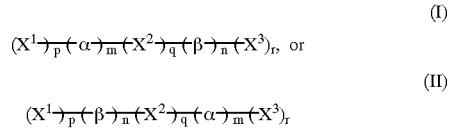

wherein the left and right ends of each of formulae (I) and (II) are, respectively, the N- and C-termini; each α is independently Phe or Trp; each β is independently Arg or Lys; each $X^1$, each $X^2$ and each $X^3$ are individually, independently an arbitrary amino acid residue; m and n are, respectively, the numbers of amino acid residues α and β; and p, q and r are, respectively, the numbers of amino acid residues $X^1$, $X^2$ and $X^3$, wherein p, q and r are the same or different; and wherein m, n, p, q and r satisfy the following requirement:

$2 \leq m+n+p+q+r \leq 10$, wherein m and n satisfy the following requirements:

$2 \leq m+n \leq 10$ and $1 \leq m, n \leq 9$, and p, q and r satisfy the following requirements:

$0 \leq p+q+r \leq 8$, $0 \leq p, r \leq 8$ and $0 \leq q \leq 5$, the peptide having an electric charge (E) satisfying the following requirement:

$+1 \leq E \leq +4$ wherein E is defined by the formula:
E=(the number of positive functional groups present in said peptide)−(the number of negative functional groups present in said peptide).

With respect to the peptide of the present invention which has an amino acid sequence represented by formula (I) or (II) above, it is requisite that the peptide contain at least one amino acid residue α selected from the group consisting of Trp and Phe (each having an aromatic hydrocarbon group as a side chain) and at least one amino acid residue β selected from the group consisting of Arg (having, as a side chain, a guanidyl group which is a positive functional group) and Lys (having, as a side chain, an amino group which is a positive functional group).

In the present invention, each of the above-mentioned amino acid residues a and D may be of either L-form or D-form.

With respect to the function of the above-mentioned amino acid residue β, it is considered that each of Arg (having, as a side chain, a guanidyl group which is a positive functional group) and Lys (having, as a side chain, an amino group which is a positive functional group) is capable of interacting electrostatically with a phosphate site present in a phospholipid of the LDL. In the present invention, it is preferred to use at least one Arg as amino acid residue β. The reason for this resides in that Arg (having a guanidyl group) has a positive charge which is higher than that of Lys so that Arg exhibits strong affinity to the LDL as compared to Lys.

The reason why the peptide of the present invention containing at least one amino acid residue α (Trp or Phe) and at least one amino acid residue β (Arg or Lys) exhibits an excellent LDL-binding ability has not yet been elucidated; however, it is considered to be as follows.

In general, it is believed that hydrophobic molecules interact with liposoluble substances, such as an LDL. As hydrophobic amino acids, there can be mentioned aliphatic amino acids, such as Ile, Leu and Val; and aromatic amino acids, i.e., Trp and Phe. In order to study the relationship between the types of amino acids contained in a peptide and the LDL-binding ability of the peptide, the present inventors have conducted comparative experiments to measure the LDL-binding ability of a peptide having Arg or Lys and having the above-mentioned hydrophobic aliphatic amino acid residue (such as Ile, Leu or Val), and the LDL-binding ability of a peptide having Arg or Lys and having the above-mentioned hydrophobic aromatic amino acid residue (i.e., Trp or Phe). As a result, it has surprisingly been found that the latter has high LDL-binding ability as compared to the former. With respect to the above-mentioned peptide having Trp or Phe, it is considered that each of Trp and Phe (each having an aromatic hydrocarbon group as a side chain) has a strong affinity to a lipid site present in the LDL as compared to an amino acid having an aliphatic hydrocarbon group as a side chain and that, therefore, the peptide containing an amino acid residue having an aromatic hydrocarbon group as a side chain is capable of exhibiting high LDL-binding ability as compared to the peptide containing an amino acid residue having an aliphatic hydrocarbon group as a side chain.

In the peptide of the present invention, which has an amino acid sequence represented by formula (I) or (II) above, there is no particular limitation with respect to the amino acid residues usable as amino acid residues $X^1$, $X^2$ and $X^3$, as long as the amino acid residues are derived from amino acids which are organic compound molecules each having at least one amino group and at least one carboxyl group. Each of amino acid residues $X^1$, $x^2$ and $X^3$ may be a residue derived from a cyclic compound which is a secondary amine formed from a non-cyclic amino acid by substituting a hydrogen atom of an amino group of the amino acid with another atom of the amino acid, or may be a residue derived from a non-protein-related amino acid. Examples of amino acids to be used to obtain amino acid residues $X^1$, $X^2$ and $X^3$ include α-amino acids, β-amino acids, γ-amino acids and δ-amino acids, each of which may be of either L-form or D-form.

Examples of L-form α-amino acids include L-alanine, L-aspartic acid, L-glutamic acid, L-phenylalanine, L-glycine, L-histidine, L-isoleucine, L-lysine, L-leucine, L-methionine, L-asparagine, L-proline, L-glutamine, L-arginine, L-serine, L-threonine, L-valine, L-tryptophan, L-tyrosine and L-cysteine.

Examples of D-form amino acids include enantiomers of the above-mentioned L-form amino acids.

Examples of non-protein-related amino acids include β-alanine, γ-aminobutyric acid, homocysteine, ornithine, 5-hydroxytryptophan, 3,4-dihydroxyphenylalanine, truiodothyronine and thyroxine.

In the present invention, the electric charge (E) is defined by the formula: E=(the number of positive functional groups present in the peptide)−(the number of negative functional groups present in the peptide).

In the present invention, the positive functional groups or the negative functional groups are functional groups which are ionized in a neutral (pH: 7.0) aqueous solution to have a positive or a negative charge. For example, the N-terminal amino group of a peptide molecule has a positive charge, whereas the C-terminal carboxyl group of a peptide molecule has a negative charge. However, the electrolytic dissociation states (ionization states) of the amino acids of a peptide in an aqueous solution vary depending on the types of the amino acids, the pH value of the aqueous solution and the like. Therefore, in the case of a certain type of amino acid residue having a functional group as a side chain, the number of ionized functional groups is determined depending on whether or not 80% or more of amino acid residues of such type are present in an ionized state in a neutral (pH: 7.0) aqueous solution of the peptide containing such an amino acid residue. For example, in the case of a peptide containing Arg having a guanidyl group as a side chain, 80% or more of Arg molecules individually contain a guanidyl group which is ionized in a neutral (pH: 7.0) aqueous solution of the peptide, so that the quanidyl group has a positive charge. Therefore, the guanidyl group of Arg is defined as a positive functional group. Also, according to the above method, the amino group present as a side chain in Lys is defined as a positive functional group. On the other hand, the carboxyl group present as a side chain in Asp or Glu is defined as a negative functional group. However, needless to say, when a functional group present in a peptide is in a non-charged state (for example, when an amino group or carboxyl group of a peptide reacts with a molecule other than the peptide molecule to form an acid-amide bond or the like therebetween, or when a functional group present in a peptide is protected by a protective group), such a functional group is not considered to be an ionized functional group.

It is requisite that the peptide of the present invention have an electric charge (E) in the range of from +1 to +4. When the electric charge (E) of the peptide is 0 or less, it is impossible for the peptide to achieve a satisfactory electrostatic interaction between the peptide and the phosphate site present in a phospholipid of an LDL, which interaction is important for binding the LDL to the peptide. Further, when the electric charge (E) is a negative value, in addition to the above disadvantage, there is a danger that the negative charge possessed by the peptide induces the production of a physiologically active substance called bradykinin in blood.

On the other hand, when the electric charge (E) of the peptide is +5 or more, disadvantages are caused such that upon contact of the peptide with blood, a strong electrostatic interaction is caused between the peptide and the blood cell components (such as erythrocyte, leukocyte and platelet) to thereby activate the blood cell components or cause the blood cell components to be adsorbed on the peptide. Further, in this case, disadvantageous phenomena occur, such as the non-specific adsorption of plasma proteins onto the peptide and the activation of a blood coagulation system, so that the peptide cannot be safely used in the LDL apheresis therapy. Therefore, in the present invention, it is requisite that the electric charge (E) of the peptide be in the range of from +1 to +4, preferably from +1 to +2.

In the present invention, it is requisite that the total number of the amino acid residues {i.e., (m+n+p+q+r) in formulae (I) and (II) above) in the peptide be at least two. In general, the larger the total number of the amino acid residues, the lower the physicochemical stability of the peptide. Specifically, a peptide containing more than 10 amino acid residues is likely to become unstable during the sterilization or the storage. Therefore, in the present invention, the peptide contains 10 amino acid residues or less. Further, from an economical point of view, it is more preferred that the peptide contains 5 amino acid residues or less.

With respect to the peptide of the present invention, which has an amino acid sequence represented by formula (I) or (II) above, the number of the amino acid residue(s) positioned between amino acid residue α (Trp or Phe) which interacts with the lipid site present in the LDL and amino acid residue β (Arg or Lys) which interacts with a negatively charged phosphate site present in the phospholipid of the LDL is especially important for the peptide to exert an excellent LDL-binding ability.

Specifically, the peptide of the present invention which is capable of binding thereto an LDL, it is requisite that the number q of amino acid residue $X^2$ be in the range of from 0 to 5. When q is 6 or more, the interaction between the peptide and the LDL, which is achieved by the cooperation of amino acid residue α with amino acid residue β lowers, so that the LDL-binding ability of the peptide becomes markedly low. For achieving high LDL-binding ability of the peptide by utilizing the effects of the cooperation of amino acid residue α with amino acid residue β, it is preferred that q is in the range of from 0 to 3.

With respect to the amino acid residues used as amino acid residues α and β, each of the amino acid residues may be of either L-form or D-form. Further, the N-terminal amino group and C-terminal carboxyl group of the peptide, and the side chains of the amino acid residues contained in the peptide, such as an amino group, a guanidyl group, an imidazolyl group, a carboxyl group, a carbamide group, a hydroxyl group, a mercapto group and an indolyl group, may be protected by a protective group.

Examples of protective groups for the N-terminal amino group of the peptide and the amino group as a side chain of the amino acid residue include a benzyloxycarbonyl (Z) group, a p-methoxybenzyloxycarbonyl {Z(OMe)} group, a p-chlorobenzyloxycarbonyl {Z(Cl)} group, a p-nitrobenzyloxycarbonyl {Z(NO₂)} group, a p-phenylazobenzyloxycarbonyl (Pz) group, a p-methoxyphenylazobenzyloxycarbonyl (Mz) group, a 3,5-dimethoxybenzyloxycarbonyl {Z(OMe)₂} group, a 3,4,5-trimethoxybenzyloxycarbonyl {Z(OMe)₃} group, a tert-butoxycarbonyl (Boc) group, a tert-amiloxycarbonyl (Aoc) group, a p-biphenylisopropyloxycarbonyl (Bpoc) group, a diisopropylmethyloxycarbonyl (Dipmoc) group, an adamantyloxycarbonyl (Adoc) group, an isobornyloxycarbonyl group, a cyclopentyloxycarbonyl (Poc) group, a cyclohexyloxycarbonyl group, a furfuryloxycarbonyl group, a benzhydryloxycarbonyl group, a piperidinoxycarbonyl group, a formyl (HCO) group, a trifluoroacetyl (Tfa) group, a phthalyl (Pht) group, a tosyl (Tos) group, an o-nitrophenylsulfenyl (Nps) group, a benzoyl (Bz) group, a chloroacetyl group, an acetoacetyl group, a trityl (Trt) group, a benzylidene group, a benzyl group, a 2-benzoyl-1-methylvinyl (Bmv) group, a trimethylsilyl (Tms) group, a 2-hydroxyallylidene group, an enamine group, a dimedone (5,5-dimethylcyclohexane-1,3-dione) group and a 9-fluorenylmethyloxycarbonyl (Fmoc) group.

Examples of protective groups for the C-terminal carboxyl group and the carboxyl group as a side chain of the amino acid residue include an amide group, a dimethylamide group, a methyl ester group (—OMe), an ethyl ester group (—OEt), a benzyl ester (—OBzl), a p-nitrobenzyl ester group {—OBzl(NO₂)}, a p-methoxybenzyl ester group, a 2,4,6-trimethylbenzyl ester group, a pentamethylbenzyl ester group, a tert-butyl ester group (—OBut), a diphenylmethyl ester group (—ODPM), a benzhydryl ester group, a trityl ester group, a phthalimidemethyl ester group, a cyclopentyl ester group, a β-methylthioethyl ester group, a β-(p-nitrothiophenyl)-ethyl ester group, a phenacyl ester group and a 4-picolyl ester group.

With respect to other side-chain functional groups of the amino acid residues, various types of protective groups can be used (see, for example, "Peputido-gousei No Kiso To Jikken (Essentials and Experiments of Peptide Synthesis)" edited by Nobuo Izumiya, Tetsuo Kato, Haruhiko Aoyagi and Michinori Waki, and published in 1985 by Maruzen Co., Ltd., Japan).

The peptide of the present invention can be synthesized by a method which is generally employed for the peptide synthesis, such as a solid phase synthesis method and a liquid phase synthesis method. However, the solid phase synthesis method is preferred from the viewpoint of ease in operation (with respect to the solid phase synthesis method, reference can be made, for example, to "Shin Seikagaku Jikken Koza 1 Tanpakushitsu IV Gousei Oyobi Hatsugen (Revised Lecture on Biochemical Experiment Vol. 1, Protein IV, Synthesis and Expression)" edited by Japanese Biochemical Society, and published in 1992 by TOKYO KAGAKU DOZIN CO., LTD., Japan}.

With respect to the synthesis by the solid phase synthesis method, detailed explanation is made below. The solid phase synthesis can be conducted by using a commercially available resin for use in the peptide synthesis, such as a divinyl benzene-containing polystyrene resin having bonded thereto a functional group having a reactivity suitable for the solid phase synthesis of a peptide, wherein a desired peptide is synthesized from the C-terminus toward the N-terminus. Specifically, for example, using the above-mentioned resin as a solid phase, the synthesis of the peptide can be conducted by a method comprising (1) a step of condensation-bonding an amino acid having a non-protected α-carboxyl group and having a functional group(s) other than the α-carboxyl group, such as an amino group, which is or are protected, to an amino acid having a non-protected α-amino group and having a functional group(s) other than the α-amino group, such as a carboxyl group, which is or are protected, to thereby obtain a condensation product; and (2) a step of removing the protective group from only the protected amino group (such as an α-amino group) of the condensation product obtained in step (1) above, wherein the protective group-removed amino group is utilized to form a peptide bond with another amino acid. Substantially the same procedure as mentioned above is repeated so as to extend the peptide chain to obtain a peptide having a desired amino acid sequence. Then, the obtained peptide is separated from the resin as the solid phase, and the protective groups are removed from all of the protected functional groups of the peptide, to thereby obtain a desired peptide. If desired, the peptide is subjected to purification to obtain a high purity peptide. The purification can be conducted by a method which is generally used for purifying an organic compound. Especially preferred is a purification method using column chromatography which is advantageous for efficiently conducting the purification.

When the peptide of the present invention is bonded directly to or indirectly through a spacer to a water-insoluble carrier, the resultant water-insoluble carrier having bonded thereto the peptide of the present invention can be used as an adsorbent for removing an LDL from a body fluid, such as ascites, a tissue fluid, whole blood and plasma. For example, the above-mentioned adsorbent can be used for removing an LDL from blood by extracorporeal blood circulation using an apparatus therefor. For example, when a apparatus utilizing the above-mentioned adsorbent is employed for the LDL apheresis of a patient suffering from familial hypercholesterolemia and the like, the LDL can be efficiently, safely removed, thus achieving high therapeutic effects. The above-mentioned adsorbent can be prepared by immobilizing the peptide on a water-insoluble carrier through the N-terminal amino group, C-terminal carboxyl group or side-chain functional group of the amino acid residue of the peptide.

More specifically, the above-mentioned adsorbent comprising a water-insoluble carrier having bonded thereto the peptide of the present invention can also be produced, for example, by a method comprising bonding to a water-insoluble carrier a group capable of forming a bond with the carrier which bond would not be cleaved even under the conditions for removing the protective groups; synthesizing a peptide by the abovementioned solid phase synthesis method using the resultant water-insoluble carrier as a solid phase to thereby obtain a water-insoluble carrier having the synthesized peptide bonded thereto; and removing the protective groups from all of the protected functional groups of the synthesized peptide.

With respect to the immobilization of the peptide on a water-insoluble carrier, the immobilization can be conducted by methods generally employed for immobilizing a peptide or a protein on a carrier. Examples of such methods include a method utilizing a carrier having a carboxyl group, in which the carboxyl group of the carrier is reacted with N-hydroxysuccinimide, to thereby convert the carboxyl group into a succinimidooxycarbonyl group, and the amino group of the peptide is reacted with the succinimidooxycarbonyl group of the carrier to thereby bond the peptide to the carrier (active esterification method); a method utilizing a carrier having an amino group or a carboxyl group, in which the carboxyl group or amino group of the peptide is subjected to condensation reaction with the amino group or carboxyl group of the carrier in the presence of a condensing agent, such as dicyclohexyl carbodiimide, to thereby bond the peptide to the carrier (condensation method); a method in which the peptide is bonded to a carrier by cross-linking reaction using a compound (such as glutaraldehyde) having at least two functional groups as a cross-linking agent (carrier cross-linking method); a method utilizing a carrier having a hydroxyl group, in which the hydroxyl group of the carrier is reacted with a cyanogen halide (such as cyanogen bromide), and the peptide is then bonded to the carrier at the amino group of the peptide; and a method in which a carrier is reacted with an epoxide (such as epichlorohydrin), and the peptide is then bonded to the carrier at an amino group or hydroxyl group of the peptide.

Further, if desired, the peptide may be indirectly bonded to a water-insoluble carrier through a molecule having an arbitrary length (i.e., a spacer). With respect to the details of the spacer, reference can be made to, for example, Kenichi Kasai et al., "Affinity Chromatography", p.105 to 108, published in 1991 by TOKYO KAGAKU DOZIN CO., LTD., Japan. By using a spacer, a desired distance can be ensured between the peptide of the present invention and a water-insoluble carrier, so that the number of the binding sites of the peptide with the LDL can be advantageously increased. Examples of spacers include a polymethylene chain and a polyethylene glycol chain. It is preferred that the length of the spacer is not more than 500 Å, more preferably not more than 200 Å. For example, when an agarose is used as a water-insoluble carrier, the binding of the peptide to the water-insoluble carrier through a spacer can be conducted by a method comprising reacting a hydroxyl group of the agarose with one of the isocyanate groups of a hexamethylene diisocyanate which is used as a spacer, reacting the remaining isocyanate group of the hexamethylene diisocyanate with an amino group, hydroxyl group or carboxyl group of the peptide to thereby bond the peptide to the carrier through the hexamethylene diisocyanate as the spacer.

In the present invention, as a preferred example of water-insoluble carriers, there can be mentioned a carrier having both a hydrophilic surface and a reactive functional group capable of forming a covalent bond with a peptide, wherein examples of such functional groups include an amino group, a carboxyl group and a hydroxyl group. Further, it is preferred that the water-insoluble carrier is a porous material having a large effective surface area usable for adsorption. When the water-insoluble carrier is a porous material, it is preferred that the exclusion limit molecular weight of the porous carrier is in the range of from 2,000,000 to 10,000,000, more preferably from 2,200,000 to 8,000,000. With respect to the water-insoluble porous carrier, it is also preferred that the average pore diameter thereof is in the range of from 20 to 100 nm, more preferably from 22 to 80 nm. The morphology of the carrier is not particularly limited and can be arbitrarily selected from various morphologies, such as particles, a fiber, a sheet and a hollow fiber.

With respect to the material for the carrier used in the present invention, there is no particular limitation, as long as it is capable of carrying a peptide on the surface thereof. The material for the carrier can be either an inorganic compound or an organic compound. As the material for the carrier, use can be made of any of those materials which are generally employed as a carrier in affinity chromatography.

Specific examples of carriers prepared from organic compounds include cellulose carriers, such as Asahi Kasei Microcarrier (manufactured and sold by Asahi Chemical Industry Co., Limited., Japan), and CM-Cellulofine CH (exclusion limit protein molecular weight: about $3 \times 10^6$; sold by SEIKAGAKU KOGYO CO., LTD., Japan); dextran carriers, such as Sephadex (manufactured and sold by Pharmacia Biotech AB, Sweden); polyvinyl alcohol carriers, such as an totally porous activated gel which is disclosed in Examined Japanese Patent Application Publication No. 1-44725 and CM-Toyopearl 650C (exclusion limit protein molecular weight: $5 \times 10^6$; manufactured and sold by Tosoh Corporation, Japan); polyacrylamide carriers, such as CM-Trisacryl M (exclusion limit protein molecular weight: $1 \times 10^7$; manufactured and sold by Pharmacia-LKB, Sweden); and agarose carriers, such as Sepharose CL-4B (exclusion limit protein molecular weight: $2 \times 10^7$; manufactured and sold by Pharmacia-LKB, Sweden). Specific examples of carriers prepared from inorganic compounds include porous glasses, such as CPG-10-1000 (exclusion limit protein molecular weight: $1 \times 10^8$; average pore diameter: 100 nm; manufactured and sold by Electro-nucleonics, U.S.A.).

The amount of the peptide bonded to the water-insoluble carrier is generally in the range of from 0.001 μmol/ml (carrier) to 1,000 μmol/ml (carrier), preferably from 0.01 μmol/ml to 500 μmol/ml, more preferably from 0.1 μmol/ml to 200 μmol/ml.

Further, when a soft gel, such as an agarose gel, or a hard gel, such as cross-linked polyvinyl alcohol, is used as the water-insoluble carrier, the adsorbent can also be used as a gel in liquid chromatography and the like for separating from a body fluid an LDL in high purity form.

With respect to the adsorbent comprising the water-insoluble carrier having bonded thereto the peptide, as a method for evaluating the binding ability (affinity) of the adsorbent for an LDL, there can be mentioned a method in which, after causing an LDL to be adsorbed on the adsorbent, the adsorbent having the LDL adsorbed thereon is subjected to staining (avidin-biotin complex method, that is, ABC method). Specifically, a biotinylated LDL is added to plasma, and the adsorbent is immersed in the plasma for a predetermined period of time. Then, the adsorbent is taken out of the plasma, and washed. Subsequently, the adsorbent is immersed in a horseradish peroxidase-labeled streptoavidin solution, and a solution of 3,3'-diamino benzidine, which is a substrate for the above-mentioned enzyme (horseradish peroxidase), is added thereto, thereby staining the adsorbent. The binding ability of the adsorbent for LDL is evaluated from the degree of the staining. With respect to methods for evaluating a binding ability for LDL, reference can be made to, for example, the following literature: S. M. Hsu, L. Raine, H. Fanger, J. Histchem. Cytochem., 29, 577 (1981); and H. Towbin, T. Staehelin, J. Gordon, Proc. Natl. Acad. Sci. U.S.A., 76, 4350 (1979).

As an example of a method for measuring the amount of an LDL which can be adsorbed on the peptide immobilized on the water-insoluble carrier, there can be mentioned a method in which a predetermined amount of an LDL is contacted with the adsorbent, and a decrease in the amount of the free LDL is measured and is taken as the amount of the LDL adsorbed on the adsorbent. Specifically, in this method, for example, the adsorbent is immersed in an LDL solution for an appropriate period of time. With respect to the LDL solution, the content of free cholesterol in the LDL solution is measured prior to and after the treatment of the LDL solution with the adsorbent to obtain a decrease ratio (%) of the free cholesterol. The decrease ratio (%) of the free cholesterol is taken as the ratio of the LDL adsorbed on the adsorbent.

Alternatively, the amount of an LDL which can be adsorbed on the adsorbent can also be determined by a method in which the adsorbent is immersed in an LDL solution, e.g., plasma, for an appropriate period of time, followed by the separation of free LDL cholesterol remaining unadsorbed from the LDL solution, and the amount of the separated LDL cholesterol is measured to thereby obtain a decrease ratio (%) of the free LDL cholesterol. The decrease ratio (%) of the free LDL cholesterol is taken as the ratio of the LDL adsorbed on the absorbent. With respect to methods for determining the amount of adsorbed LDL, reference can be made to, for example, the following literature: Richmond W., Scand. J. Clin. Lab. Invest., 29 (suppl.), 126 (1972); and Allain, C. C., Poon, L. S., Chan, C. S. G., Richmond, W. and Fu, P. C., Clin. Chem., 20, 470–475 (1974).

Further, the binding ability (affinity) of the adsorbent for an LDL can also be determined by using BIAcore (manufactured and sold by Pharmacia Biosensor AB, Sweden), in accordance with the instructions given in a manual attached to BIAcore. Specifically, the binding ability of the adsorbent for an LDL can also be determined by a method in which the peptide is immobilized on a sensor chip of the BIAcore, and a solution containing LDL, such as plasma, is flowed over the sensor chip.

BEST MODE FOR CARRYING OUT THE INVENTION

Hereinbelow, the present invention will be described in more detail with reference to the following Examples and Comparative Examples, but they should not be construed as limiting the scope of the present invention.

EXAMPLE 1 AND COMPARATIVE EXAMPLE 1

Five different peptides, each composed of 5 amino acid residues, were synthesized from L-form Fmoc-amino acids by solid phase method using a multipeptide synthesizing system (RaMPS; manufactured and sold by NEN Research Products, U.S.A.), in accordance with the instructions given in a manual attached to the system. In the synthesis, a polystyrene resin having bonded thereto a polyethylene glycol chain having at a terminal thereof an amino group (TG resin; manufactured and sold by Calbiochem-Novabiochem Corp, U.S.A.) was used as a solid phase.

In Example 1, the five different peptides (SEQ ID NOS. 1–5) were individually prepared so as to have the following characteristics (1) to (3):

(1) each peptide contains, at a predetermined position thereof, one amino acid residue β (R or K) having a positive functional group as a side chain;

(2) each peptide contains, at an arbitrary position thereof which is other than the position of amino acid residue β mentioned in (1) above, one amino acid residue α (W or F) having an aromatic hydrocarbon group as a side chain; and (3) each peptide contains, respectively at 3 positions thereof which are other than the position of amino acid residue β mentioned in (1) above and the position of amino acid residue α mentioned in (2) above, 3 amino acid residues, which are individually selected from the group consisting of 20 L-form, protein-related amino acid residues, wherein the 3 amino acid residues are chosen so that the peptide has an electric charge (E) of +1.

The amino acid sequences of the peptides obtained in Example 1 are shown in Table 1 below, wherein N1 to N5 indicate the first to fifth amino acids, respectively.

In Comparative Example 1, in substantially the same manner as mentioned above in connection with Example 1, five different peptides (SEQ ID NOS: 62–66) having amino acid sequences as also shown in Table 1 below (wherein N1 to N5 have the same meanings as mentioned above) were individually prepared so as to have the following characteristics (1') to (3'):

(1') each peptide contains, at a predetermined position thereof, one amino acid residue β (R or K) having a positive functional group as a side chain;

(2') each peptide contains, at an arbitrary position thereof which is other than the position of amino acid residue β mentioned in (1') above, one amino acid residue selected from the group consisting of V, L and F, which are L-form, protein-related amino acid residues having an aliphatic hydrocarbon group as a side chain; and (3') each peptide contains, respectively at 3 positions thereof which are other than the position of amino acid residue β mentioned in (1') above and the position of the amino acid residue mentioned in (2') above, 3 amino acid residues, which are individually selected from the group consisting of 18 amino acid residues (of 20 L-form, protein-related amino acid residues exclusive of W and F as amino acid residue α), wherein the 3 amino acid residues are chosen so that the peptide has an electric charge (E) of +1.

The ability of each of the peptides to bind thereto an LDL was evaluated as follows. To a blood sample obtained from a healthy person was added a 3.8% aqueous solution of sodium citrate to thereby obtain a mixture. The obtained mixture was centrifuged to separate the blood sample into a blood cells component and a plasma component. To the obtained plasma component was added a solution containing an LDL (manufactured and sold by Sigma Chemical Company, U.S.A) which was biotinylated using a biotinylation kit (manufactured and sold by Amersham International, England) (the biotinylation was conducted according to the instructions given in a manual attached to the biotinylation kit) in an amount such that the final concentration of the LDL in the resultant plasma-LDL mixture became 10 mg/ml.

On the other hand, each of the above-mentioned polystyrene resins having bonded thereto the above-synthesized peptides was individually taken out from the synthesis reaction system and packed in a column having a filter (manufactured and sold by Bio-Rad laboratories, U.S.A.). Subsequently, the plasma-LDL mixture prepared above was added to the column, and the column was allowed to stand at room temperature for 1 hour. Then, the column was washed with a physiological saline containing 0.1% Tween 20 and sodium phosphate. After the washing, 1 ml of a horseradish peroxidase-labeled streptoavidine (0.2 ug/ml) solution containing 10% Block Ace (manufactured and sold by Dainippon Pharmaceutical Co., Ltd., Japan) was added to the column, and the column was allowed to stand at room temperature for 30 minutes. Then, 1 ml of a 3,3'-diaminobenzidine tetrahydrochloride (0.5 g/ml) solution containing 0.005% hydrogen peroxide was added to the column (by the addition of this solution, when a peptide-bonded resin contained in the column has the LDL bonded thereto, the resin is stained to assume brown color).

Results are shown in Table 1, wherein the peptide-bonded resins which were stained are indicated with "+ (plus)" and the peptide-bonded resins which were not stained are indicated with "– (minus)".

As can be seen from Table 1, all of the peptide-bonded resins prepared in Example 1 were stained, whereas none of the peptide-bonded resins prepared in Comparative Example 1 were stained. This clearly shows that the peptides containing β (R and/or K) and α (W and/or F, which is an amino acid residue having an aromatic hydrocarbon group as a side chain) are capable of binding thereto an LDL.

EXAMPLE 2 AND COMPARATIVE EXAMPLE 2

Fourteen different peptides, each composed of 5 amino acid residues, were synthesized from L-form, Fmoc-amino acids by solid phase method using a multipeptide synthesizing system (RaMPS; manufactured and sold by NEN Research Products, U.S.A.), in accordance with the instructions given in a manual attached to the system. In the synthesis, a polystyrene resin having bonded thereto a polyethylene glycol chain having at a terminal thereof an amino group (TG resin; manufactured and sold by Calbiochem-Novabiochem Corp., U.S.A.) was used as a solid phase.

In Example 2, the fourteen different peptides (SEQ ID NOS: 6–19) were individually prepared so as to have the following characteristics (1) to (3):

(1) each peptide contains, at a predetermined position thereof, one amino acid residue β (R or K) having a positive functional group as a side chain;

(2) each peptide contains, at an arbitrary position thereof which is other than the position of amino residue β mentioned in (1) above, one amino acid residue α (W or F) having an aromatic hydrocarbon group as a side chain; and (3) each peptide contains, respectively at 3 positions thereof which are other than the position of amino residue β mentioned in (1) above and the position of amino residue α mentioned in (2) above, 3 amino acid residues, which are individually selected from the group consisting of 20 L-form, protein-related amino acid residues, wherein the 3 amino acid residues are chosen so that the peptide has an electric charge (E) of from +1 to +4.

The amino acid sequence of the peptides obtained in Example 2 are shown in Table 2 below, wherein N1 to N5 indicate the first to fifth amino acids, respectively.

In Comparative Example 2, in substantially the same manner as mentioned above in connection with Example 2, fourteen different peptides (SEQ ID NOS: 67–80) having amino acid sequences as also shown in Table 2 below (wherein N1 to N5 have the same meanings as mentioned above) were individually prepared so as to have the following characteristic (1'):

(1') each peptide contains 5 amino acid residues which are individually selected from the group consisting of 20 L-form, protein-related amino acid residues, wherein the 5 amino acid residues are chosen so that the peptide does not satisfy either of the following requirements a and b:

a: the peptide should contain amino acid residue α (W or F) and amino acid residue β (R or K); and b: the peptide should have an electric charge (E) of from +1 to +4.

The ability of each of the peptides to bind thereto an LDL was evaluated in substantially the same manner as in Example 1. Results are shown in Table 2.

As can be seen from Table 2, all of the peptide-bonded resins prepared in Example 2 were stained, whereas none of the peptide-bonded resins prepared in Comparative Example 2 were stained. This clearly shows that the peptides synthesized in Example 2 are capable of binding thereto an LDL.

EXAMPLE 3 AND COMPARATIVE EXAMPLE 3

Four different peptides and two different comparative peptides (which are all shown in Table 3) were synthesized from L-form, Fmoc-amino acids by solid phase method using a multipeptide synthesizing system (RaMPS; manufactured and sold by NEN Research Products, U.S.A.), in accordance with the instructions given in a manual attached to the system. In the synthesis, a polystyrene resin having bonded thereto a polyethylene glycol chain having at a terminal thereof an amino group (TG resin; manufactured and sold by Calbiochem-Novabiochem Corp., U.S.A.) was used as a solid phase.

In Example 3, four different peptides (SEQ ID NOS: 20–23) each bonded to the above-mentioned polystyrene resin were individually prepared so as to have amino acid sequences WAWRR, LFLMR, WAWRRGGGGG and LFLMRGGGGG, respectively.

In Comparative Example 3, in substantially the same manner as mentioned above in connection with Example 3, two different peptides each bonded to the above-mentioned polystyrene resin were individually prepared so as to have amino acid sequences WAWEEGGGGG and FFFFFGGGGG (SEQ ID NOS: 81 and 82), respectively, wherein each of the two peptides has an electric charge (E) of 0 or less.

With respect to each of the peptide-bonded resins prepared in Example 3 and Comparative Example 3, the LDL-adsorbing ratio was measured as follows. To the peptide-bonded resin (85 mg as measured in a dry state thereof) was added a phosphate-buffered physiological saline (hereinafter, frequently referred to as "PBS") to thereby swell the resin. The obtained swollen resin was immersed in 1 ml of an LDL solution (50 µg/ml) prepared by diluting an LDL (manufactured and sold by Sigma Chemical Company, U.S.A.) with PBS. With respect to the LDL solution, the concentration of free cholesterol was measured prior to and after the treatment of the LDL solution with the swollen peptide-bonded resin to obtain a decrease ratio (%) of the free cholesterol. The measurement of the concentration of free cholesterol was conducted by means of Cholesterol E-Test Wako (manufactured and sold by Wako Pure Chemical Industries Ltd., Japan) in accordance with the instructions given in a manual attached thereto. The decrease ratio (%) of the free cholesterol was taken as the LDL-adsorbing ratio. Results are shown in Table 3.

As can be seen from Table 3, none of the peptides synthesized in Comparative Example 3 had satisfactory LDL-binding ability, whereas all of the peptides synthesized in Example 3 had excellent LDL-binding ability.

EXAMPLE 4

Six different peptides were synthesized from L-form, Fmoc-amino acids by solid phase method using a multipeptide synthesizing system (RaMPS; manufactured and sold by NEN Research Products, U.S.A.), in accordance with the instructions given in a manual attached to the system. In the synthesis, a polystyrene resin having bonded thereto a polyethylene glycol chain having at a terminal thereof an amino group (TG resin; manufactured and sold by Calbiochem-Novabiochem Corp., U.S.A.) was used as a solid phase.

Specifically, six different peptides each bonded to the above-mentioned polystyrene resin were individually prepared using L-form, Fmoc-amino acids so as to have amino acid sequences WWR, WWK, WFWR, WFWK, WFWRR and WFWKK, respectively (the latter four being SEQ ID NOS:24–27).

With respect to each of the obtained peptide-bonded resins, the LDL-adsorbing ratio was measured as follows. To the peptide-bonded resin (85 mg as measured in a dry state thereof) was added PBS to thereby swell the resin. The obtained swollen resin was immersed in 1 ml of an LDL solution (50 µg/ml) prepared by diluting an LDL (manufactured and sold by Sigma Chemical Company, U.S.A.) with PBS. With respect to the LDL solution, the concentration of free cholesterol was measured prior to and after the treatment of the LDL solution with the swollen peptide-bonded resin to obtain a decrease ratio (%) of the free cholesterol. The measurement of the concentration of free cholesterol was conducted by means of Cholesterol E Test Wako (manufactured and sold by Wako Pure Chemical Industries Ltd., Japan) in accordance with the instructions given in a manual attached thereto. The decrease ratio (%) of the free cholesterol concentration was taken as the LDL-adsorbing ratio. Results are shown in Table 4.

As can be seen from Table 4, all of the peptides synthesized in Example 4 had excellent LDL-binding ability.

EXAMPLE 5

Eight different peptides were synthesized by solid phase method using a multipeptide synthesizing system (RaMPS; manufactured and sold by NEN Research Products, U.S.A.), in accordance with the instructions given in a manual attached to the system. In the synthesis, a polystyrene resin having bonded thereto a polyethylene glycol chain having at a terminal thereof an amino group (TG resin; manufactured and sold by Calbiochem-Novabiochem Corp., U.S.A.) was used as a solid phase.

Specifically, four different peptides each bonded to the above-mentioned polystyrene resin were individually prepared from D-form, Fmoc-amino acids so as to have amino acid sequences WR, WWR, WWWR (SEQ ID NO:28) and WFWRR, respectively, and further four different peptides each bonded to the above-mentioned polystyrene resin were individually prepared from L-form, Fmoc-amino acids so as to have amino acid sequences WR, WWR, WWWR, and WFWRR, respectively.

The LDL-adsorbing ratio of each of the peptide-bonded resin was measured in substantially the same manner as in Example 4. Results are shown in Table 5.

As can be seen from Table 5, all of the peptides synthesized in Example 5 had excellent LDL-binding ability.

EXAMPLE 6

Six different peptides (shown in Table 6) were synthesized from L-form, Fmoc-amino acids by solid phase method using a multipeptide synthesizing system (RaMPS; manufactured and sold by NEN Research Products, U.S.A.), in accordance with the instructions given in a manual attached to the system (the latter four being SEQ ID NOS:29–32). In the synthesis, a polystyrene resin having bonded thereto a polyethylene glycol chain having at a terminal thereof an amino group (TG resin; manufactured and sold by Calbiochem-Novabiochem Corp., U.S.A.) was used as a solid phase. The LDL-adsorbing ratio of each of the peptide-bonded resins was measured in substantially the same manner as in Example 4. Results are shown in Table 6.

As can be seen from Table 6, all of the peptides synthesized in Example 6 had excellent LDL-binding ability.

EXAMPLE 7 AND COMPARATIVE EXAMPLE 4

Two different peptides were synthesized by solid phase method using an automatic peptide synthesizer (9050 plus peptide synthesizer: sold by Nihon PerSeptive Ltd., Japan). Illustratively stated, peptides were produced from L-form, Fmoc-amino acids according to the conventional methods, using a granular resin (Fmoc-PAL-PEG-PS: sold by Nihon PerSeptive Ltd., Japan) comprising a styrene-divinylbenzene copolymer containing 4-aminomethyl-3,5-dimethoxyphenoxymethyl group in an amount of 0.18 mmol per gram of the resin.

In Example 7, a first peptide having an amidated C-terminus, which has an amino acid sequence of WFWRK-$CONH_2$ (SEQ ID NO:33), was prepared.

The prepared peptide was analyzed by high performance liquid chromatography (HPLC) using a reversed phase column (TSK gel ODS-80TM; manufactured and sold by Tosoh Corp., Japan), wherein the absorbance at a wavelength of 220 nm was measured. As a result, a single peak was observed at the wavelength of 220 nm.

Further, in Example 7, in substantially the same manner as mentioned above, a second peptide having an amidated C-terminus, which has an amino acid sequence of KRWFW-$CONH_2$ (SEQ ID NO:34) was prepared from L-form amino acids.

In Comparative Example 4, in substantially the same manner as in Example 7, two different peptides each having an amidated C-terminus, which respectively have an amino acid sequence of QDGSDEVYK-$CONH_2$ (SEQ ID NO:83) and an amino acid sequence of QGDDSEVYK-$CONH_2$ (SEQ ID NO:84) were prepared from L-form amino acids.

With respect to each of the peptides synthesized in Example 7 (i.e., WFWRK-$CONH_2$ and KRWFW-$CONH_2$) and to each of the peptides synthesized in Comparative Example 4 (i.e., QDGSDEVYK-$CONH_2$ and QGDDSEVYK-$CONH_2$), the affinity thereof to the LDL was evaluated as follows. 10 μl of a peptide solution (1 mmol/liter) was added to 90 μl of a solution of an LDL (5 mg/ml) (manufactured and sold by Sigma Chemical Company, U.S.A.) to thereby obtain a mixture, and the obtained mixture was incubated at room temperature for 1 hour. Then, the incubated mixture was filtered through an ultrafiltration membrane (ULTRAFREE MC PLGC; manufactured and sold by MILLIPORE, U.S.A.) by centrifugation. The resultant filtrate containing free peptides was subjected to high performance liquid chromatography (HPLC) using a reversed phase column (OD Cosmosil 5C18; manufactured and sold by Nacalai Tesque, Japan), to thereby separate the peptide having the LDL bonded thereto. With respect to the separated peptide, the absorbance at the wave length of 275 nm was measured. The LDL-binding ratio (%) of the peptide was calculated from the difference between the height of the HPLC peak obtained with respect to the above-mentioned peptide having the LDL bonded thereto and the height of the HPLC peak obtained with respect to an LDL-free peptide, wherein the HPLC peak of the LDL-free peptide was obtained in substantially the same manner as in the case of the peptide having the LDL bonded thereto except that a buffer containing no LDL was used instead of the LDL solution. Results are shown in Table 7. From the results, it is apparent that the peptides prepared in Example 7 are superior to the peptides prepared in Comparative Example 4 with respect to the affinity to the LDL.

EXAMPLE 8 AND COMPARATIVE EXAMPLE 5

In Example 8, the two different peptides prepared in Example 7, which respectively have an amino acid sequence of WFWRK-$CONH_2$ and an amino acid sequence of KRWFW-$CONH_2$, were individually immobilized on a cyanide bromide-activated Sepharose (manufactured and sold by Pharmacia-LKB, Sweden) (hereinbelow, frequently referred to simply as "gel") in accordance with conventional methods. In Comparative Example 5, the peptide having an amino acid sequence of QDGSDEVYK-$CONH_2$ prepared in Comparative Example 4 was immobilized on the same gel (i.e., cyanide bromide-activated Sepharose) as employed in Example 8, in the same manner as in Example 8. Illustratively stated, with respect to each of the three different peptides prepared in Example 7 and Comparative Example 4, the following procedure was performed. An appropriate amount of the above-mentioned gel was washed with 1 mM hydrogen chloride solution to obtain a washed swollen gel. 10 mg of a purified peptide was dissolved in 0.1 M sodium carbonate buffer (pH 8.4) containing 0.5 M sodium chloride to thereby obtain a peptide solution, and the obtained peptide solution was added to 8 ml of the swollen gel and a reaction was performed for 2 hours. After the reaction, the gel was transferred to 1 M ethanolamine solution (prepared so that the pH value of the solution became 8) to terminate the reaction, thereby obtaining a peptide-immobilized gel. In this way, three different peptide-immobilized gels were obtained.

With respect to each of the peptide-immobilized gels obtained in Example 8 and Comparative Example 5, the LDL-adsorbing ratio of the peptide immobilized on the gel was evaluated as follows.

A peptide-immobilized gel was washed with PBS to obtain a swollen, peptide-immobilized gel. 250 μl of the obtained swollen, peptide-immobilized gel was immersed in 500 μl of an LDL solution (200 μg/ml) prepared by diluting an LDL (manufactured and sold by Sigma Chemical Company, U.S.A.) with PBS. With respect to the LDL solution, the concentration of free cholesterol in the LDL solution was measured prior to and after the treatment of the LDL solution with the swollen, peptide-immobilized gel to obtain a decrease ratio (%) of the free cholesterol. The measurement of the concentration of the free cholesterol in the LDL solution was performed by means of Cholesterol E-Test WAKO (manufactured an sold by WAKO PURE CHEMICAL Industries Ltd., Japan) in accordance with the instructions given in a manual attached thereto. The decrease ratio of the free cholesterol was taken as the LDL-adsorbing ratio of the peptide immobilized on the gel. Results are shown in Table 8. From the results, it is apparent that the LDL-binding abilities of the peptides immobilized on gel in Example 8 are extremely high, as compared to that of the peptide immobilized on gel in Comparative Example 5.

EXAMPLE 9 AND COMPARATIVE EXAMPLE 6

In Example 9, use was made of the same peptide-immobilized gels as obtained in Example 8, i.e., two different peptide-immobilized gels obtained by a method in which the two different peptides prepared in Example 7, which respectively have an amino acid sequence of WFWRK- CONH$_2$ and an amino acid sequence of KRWFW-CONH$_2$, are individually immobilized on a cyanide bromide-activated Sepharose (manufactured and sold by Pharmacia-LKB, Sweden). In Comparative Example 6, a commercially available dextran sulfate-immobilized cellulose was used. Specifically, in Example 9 and Comparative Example 6, with respect to each of the same peptide-immobilized gels as obtained in Example 8, and to a commercially available dextran sulfate-immobilized cellulose, the influence of the ligand (i.e., each of the peptide and the dextran sulfate) on bradykinin production in plasma was evaluated by the following method.

A blood sample was obtained from a healthy person, and heparin was added thereto (10 IU/ml). Then, the blood sample was centrifuged to separate a plasma component. To the obtained plasma component was added captopril (50 ng/ml) (manufactured and sold by Sigma Chemical Company, U.S.A.) to thereby obtain a mixture, and 5 ml of the obtained mixture was added to 1 ml of a swollen gel (i.e., a peptide-immobilized gel in a swollen state or a dextran sulfate-immobilized cellulose in a swollen state) placed in an Erlenmeyer flask made of polycarbonate, and the Erlenmeyer flask was then allowed to stand at 37° C. for 5 minutes.

Subsequently, the plasma component was immediately separated from the gel, and 2 ml of an inhibitor solution containing trasylol (aprotinin), soy bean trypsine inhibitor, protamine sulfate and EDTA-2Na was added to the plasma component to terminate the reaction. The amount of bradykinin produced in the plasma was measured by RIA (radioimmunoassay).

For obtaining control data, substantially the same procedure as mentioned above was repeated twice, except that, in a first repetition, no gel was used (and only the same polycarbonate flask as mentioned above was used), and that, in a second repetition, no gel was used, and a glass flask, which is believed to markedly promote bradykinin production, is used instead of the polycarbonate flask. Results are shown in Table 9. From the results, it is apparent that the amount of bradykinin produced in the presence of any of WFWRK-CONH$_2$-immobilized Sepharose and KRWFW-CONH$_2$-immobilized Sepharose is comparable to or smaller than the amounts of bradykinin produced in the control experiments conducted in the absence of a gel.

EXAMPLE 10 AND COMPARATIVE EXAMPLE 7

In Example 10, two peptides (samples 1 and 2) each bonded to a resin, which respectively have an amino acid sequence of WFWRK and an amino acid sequence of KRWFW, were synthesized in substantially the same manner as in Example 7, except that the solid phase synthesis was conducted using as a solid phase (resin) a granular resin comprising a styrene-divinylbenzene copolymer (PAC-PEG-PS; manufactured and sold by Nihon PerCeptive Ltd., Japan). With respect to the resultant resin having the peptide bonded thereto, the affinity for blood cells was evaluated in accordance with a method described below.

In Comparative Example 7, a peptide having an amino acid sequence of VVWRLTRKRGLKVVV (SEQ ID NO:85) was synthesized in substantially the same manner as in Example 7, except that the solid phase synthesis was conducted using as a solid phase (resin) a granular resin comprising a styrene-divinylbenzene copolymer (PAC-PEG-PS; manufactured and sold by Nihon PerSeptive Ltd., Japan).

Using polylysine (average molecular weight: 53,900; manufactured and sold by Sigma Chemical Company, U.S.A.) and the peptide (VVWRLTRKRGLKVVV) obtained above, a polylysyine-immobilized gel and a peptide (VVWRLTRKRGLKVVV)-immobilized gel were individually prepared in substantially the same manner as in Example 8. With respect to each of the obtained polylysine-immobilized gel (comparative sample 1) and the obtained peptide-immobilized gel (comparative sample 2), the affinity to blood cells was evaluated in accordance with a method described below.

In each of Example 10 and Comparative Example 7, the evaluation of the affinity of the peptide (or polylysine)-bonded resin was conducted as follows. A blood sample prepared by adding 1 IU/ml of heparin to blood obtained from a healthy person was added to 0.5 ml of the peptide (or polylysine)-bonded resin which had been swelled with physiological saline. The resultant mixture was allowed to stand at 37° C. for 30 minutes. Subsequently, the resin was separated from the mixture, followed by washing with physiological saline. The resultant resin was visually observed. Results are shown in Table 10. With respect to comparative samples 1 and 2, each having an electric charge (E) of +5 or more, the occurrence of adhesion of blood cells to the resin or the occurrence of blood aggregation was observed. On the other hand, with respect to samples 1 and 2 (the WFWRK-bonded Sepharose and the KRWFW-bonded Sepharose, respectively), almost no occurrence of adhesion of blood cells to the resin was observed.

EXAMPLE 11 AND COMPARATIVE EXAMPLE 8

Twenty-six different peptides and four different comparative peptides (which are all shown in Table 11; wherein for Example 11, Sample Nos. 1, 4 and 5–26 are SEQ ID NOS:35, 89 and 36–57, respectively, and wherein for Comparative Example 8, Sample Nos. 1, 2, 3 and 4 are SEQ ID NOS:86, 87, 90 and 88, respectively) were prepared in substantially the same manner as in Example 7. Each of the obtained peptides was individually dissolved in a 10 mM acetate buffer (pH: 5.5) to thereby obtain peptide solutions each having a peptide concentration of $3.5 \times 10^{-3}$ mol/ml. Then, 35 µl of each peptide solution was individually injected to BIAcore (manufactured and sold by Pharmacia Biosensor AB, Sweden) equipped with an activated sensor chip CM5 Certified (manufactured and sold by Pharmacia Biosensor AB, Sweden) (hereinafter, frequently referred to simply as "sensor chip") to thereby immobilize the peptide on the sensor chip by amino coupling, in accordance with the instructions given in a manual attached to the BIAcore. The flow rate of the peptide solution for the immobilization of the peptide was 5 µl/min. After the immobilization of the peptide, ethanolamine was injected into the BIAcore to thereby block the unreacted active sites remaining on the sensor chip. Then, the sensor chip was washed with HBS buffer (described in the manual attached to the BIAcore) until the base line for the sensor chip became stable.

The affinity of the peptide to the LDL contained in HBS buffer was measured using the above-mentioned BIAcore (provided with the sensor chip having the peptide immobilized thereon) as follows. 60 µl of an LDL solution was injected into the BIAcore over 6 minutes. The flow rate of the LDL solution was 10 µl/min. The affinity of the peptide to the LDL was obtained as a difference between the RU (Resonance Unit) value corresponding to the base line and the RU value obtained at the time of 10 seconds before the completion of the 6-minute injection of the LDL solution.

However, since the amounts of the peptides immobilized on the sensor chip vary depending on the types of the peptides, the amount of a peptide of RRWFW-CONH$_2$ immobilized on the sensor chip was taken as a standard amount and the affinities of various tested peptides were determined, based on the above standard amount. Results of the measurements are shown in Table 11. Table 11 clearly shows that the peptides prepared in Example 11 are superior to the peptides prepared in Comparative Example 8 with respect to the affinity to the LDL.

EXAMPLE 12 AND COMPARATIVE EXAMPLE 9

Twenty-seven different peptides and four different comparative peptides (which are all shown in Table 12, wherein for Example 12, Sample Nos. 12–15 are SEQ ID NOS:12–15, respectively) were prepared in substantially the same manner as in Example 7. Each of the obtained peptides was individually dissolved in a 10 mM acetate buffer (pH: 5.5) to thereby obtain peptide solutions each having a peptide concentration of $3.5 \times 10^{-3}$ mol/ml. Then, 35 µl of each peptide solution was individually injected to BIAcore (manufactured and sold by Pharmacia Biosensor AB, Sweden) equipped with an activated sensor chip CM5 Certified (manufactured and sold by Pharmacia Biosensor AB, Sweden) (hereinafter, frequently referred to simply as "sensor chip") to thereby immobilize the peptide on the sensor chip by amino coupling, in accordance with the instructions given in a manual attached to the BIAcore. The flow rate of the peptide solution for the immobilization of the peptide was 5 µl/min. After the immobilization of the peptide, ethanolamine was injected into the BIAcore to thereby block the unreacted active sites remaining on the sensor chip. Then, the sensor chip was washed with HBS buffer (described in the manual attached to the BIAcore) until the base line for the sensor chip became stable.

The affinity of the peptide to the LDL in plasma was measured using the above-mentioned BIAcore (provided with the sensor chip having the peptide immobilized thereon) as follows. 60 µl of LDL-free plasma was injected into the BIAcore over 6 minutes and, then, plasma containing 1 mg/ml of LDL was injected into the BIAcore over 6 minutes. The flow rate of these two types of plasma was 10 µl/min. An example of profiles obtained by the measurement of the affinity of the peptide to the LDL using BIAcore is shown in FIG. 1.

The affinity of the peptide to the LDL was obtained as a difference between the RU (Resonance Unit) value obtained at the time of 10 seconds before the completion of the 6-minute injection of the LDL-free plasma (indicated by "A" in FIG. 1) and the RU value obtained immediately after achieving complete replacement of the LDL-containing plasma by HBS buffer (namely, at the time of 6 minutes and 10 seconds after the start of the 6-minute injection of the LDL-containing plasma (indicated by "B" in FIG. 1). However, since the amounts of the peptides immobilized on the sensor chip vary depending on the types of the peptides, the amount of a peptide of RRWFW-CONH$_2$ immobilized on the sensor chip was taken as a standard amount and the affinities of various tested peptides were determined, based on the above standard amount. Results of the measurements are shown in Table 12. Table 12 clearly shows that the peptides prepared in Example 12 are superior to the peptides prepared in Comparative Example 9 with respect to the affinity to the LDL.

EXAMPLE 13 AND COMPARATIVE EXAMPLE 10

In Example 13, four different peptides respectively having amino acid sequences RRWFW-CONH$_2$, RRWAW-CONH$_2$, RRWEW-CONH$_2$ and RRWRW-CONH$_2$) were prepared in substantially the same manner as in Example 7. The obtained peptides were individually immobilized on a cyanide bromide-activated Sepharose (manufactured and sold by Pharmacia-LKB, Sweden) (hereinbelow, frequently referred to simply as "gel") in accordance with the conventional methods. In Comparative Example 10, the peptide having an amino acid sequence of QDGSDEVYK-CONH$_2$ prepared in Comparative Example 4 was immobilized on the same gel (i.e., cyanide bromide-activated Sepharose) as employed in Example 13, in the same manner as in Example 13. Illustratively stated, with respect to each of five different peptides prepared in Example 13 and Comparative Example 10, the following procedure was performed. An appropriate amount of the above-mentioned gel was washed with 1 mM hydrogen chloride solution to obtain a washed swollen gel. 10 mg of a purified peptide was dissolved in 0.1 M sodium carbonate buffer (pH 8.4) containing 0.5 M sodium chloride to thereby obtain a peptide solution, and the obtained peptide solution was added to 8 ml of the swollen gel and a reaction was performed for 2 hours. After the reaction, the gel was transferred to 1 M ethanolamine solution (prepared so that the pH value of the solution became 8) to terminate the reaction, thereby obtaining a peptide-immobilized gel. In this way, five different peptide-immobilized gels were obtained.

With respect to each of the peptide-immobilized gels obtained in Example 13 and Comparative Example 10, the LDL-adsorbing ratio of the peptide immobilized on the gel was evaluated as follows.

A peptide-immobilized gel was washed with PBS to obtain a swollen, peptide-immobilized gel. 250 µl of the obtained swollen, peptide-immobilized gel was immersed in 1 ml of plasma obtained from a healthy person. Subsequently, free LDL cholesterol remaining unadsorbed in the plasma was separated from the plasma by means of an LDL cholesterol separation kit (manufactured and sold by SIGMA DIAGNOSTICS, U.S.A.), and the amount of the separated LDL cholesterol was measured to thereby obtain a decrease ratio (%) of the free LDL cholesterol. The measurement of the content of the free LDL cholesterol in the plasma was performed by means of Cholesterol E-Test WAKO (manufactured an sold by WAKO PURE CHEMICAL Industries Ltd., Japan) in accordance with the instructions given in a manual attached thereto. The decrease ratio (%) of the free LDL cholesterol was taken as the LDL-adsorbing ratio of the peptide immobilized on the gel. Results are shown in Table 13. From the results, it is apparent that the peptides immobilized on the gel in Example 13 are superior to the peptide immobilized on gel in Comparative Example 10 with respect to the LDL-binding ability.

TABLE 1

| Sample No. | N1 | N2 | N3 | N4 | N5 | Electric charge (E) | Stain |
|---|---|---|---|---|---|---|---|
| Example 1 | | | | | | | |
| 1 | R | F | Y | Y | M | +1 | + |
| 2 | F | K | I | W | W | +1 | + |
| 3 | W | Q | R | H | F | +1 | + |
| 4 | I | F | Y | K | W | +1 | + |
| 5 | W | A | L | Y | R | +1 | + |

TABLE 1-continued

| Sample No. | N1 | N2 | N3 | N4 | N5 | Electric charge (E) | Stain |
|---|---|---|---|---|---|---|---|
| Comparative Example 1 | | | | | | | |
| 1 | R | A | H | I | N | +1 | − |
| 2 | P | K | S | I | N | +1 | − |
| 3 | L | H | R | H | L | +1 | − |
| 4 | L | T | M | K | M | +1 | − |
| 5 | M | L | T | V | R | +1 | − |

TABLE 2

| Sample No. | N1 | N2 | N3 | N4 | N5 | Electric Charge (E) | Stain |
|---|---|---|---|---|---|---|---|
| Example 2 | | | | | | | |
| 1 | W | T | A | R | R | +2 | + |
| 2 | F | A | Y | R | R | +2 | + |
| 3 | R | W | I | L | Q | +1 | + |
| 4 | R | F | W | L | F | +1 | + |
| 5 | R | Y | A | F | W | +1 | + |
| 6 | K | H | I | Y | W | +1 | + |
| 7 | W | R | Y | D | R | +1 | + |
| 8 | L | K | W | F | Q | +1 | + |
| 9 | Y | Y | R | W | F | +1 | + |
| 10 | L | W | K | S | F | +1 | + |
| 11 | F | F | W | R | G | +1 | + |
| 12 | L | N | F | R | W | +1 | + |
| 13 | F | L | M | R | F | +1 | + |
| 14 | W | L | M | W | R | +1 | + |
| Comparative Example 2 | | | | | | | |
| 1 | T | H | R | Q | R | +2 | − |
| 2 | H | Y | Y | L | Q | ±0 | − |
| 3 | W | H | V | Q | T | ±0 | − |
| 4 | P | N | A | F | A | ±0 | − |
| 5 | H | W | V | V | H | ±0 | − |
| 6 | Y | I | Q | V | W | ±0 | − |
| 7 | F | G | A | I | V | ±0 | − |
| 8 | H | A | S | N | P | ±0 | − |
| 9 | E | W | S | M | T | −1 | − |
| 10 | F | I | I | M | E | −1 | − |
| 11 | W | V | D | H | N | −1 | − |
| 12 | E | A | K | H | E | −1 | − |
| 13 | F | N | F | E | S | −1 | − |
| 14 | V | E | E | M | E | −3 | − |

TABLE 3

| Sample | LDL-adsorbing ratio (%) |
|---|---|
| Example 3 | |
| 1. WAWRR | 62.2 |
| 2. LFLMR | 39.3 |
| 3. WAWRRGGGGG | 49.8 |
| 4. LFLMRGGGGG | 36.9 |
| Comparative Example 3 | |
| 1. WAWEEGGGGG | 4.3 |
| 2. FFFFFFGGGGG | 2.6 |

TABLE 4

| Sample | LDL-adsorbing ratio (%) |
|---|---|
| 1. WWR | 32.0 |
| 2. WWK | 25.0 |
| 3. WFWR | 35.0 |
| 4. WFWK | 33.0 |
| 5. WFWRR | 49.0 |
| 6. WFWKK | 43.0 |

TABLE 5

| Sample | LDL-adsorbing ratio (%) |
|---|---|
| 1. WR (D-form) | 38.6 |
| 2. WWR (D-form) | 41.6 |
| 3. WWWR (D-form) | 33.8 |
| 4. WFWRR (D-form) | 38.3 |
| 5. WR (L-form) | 27.7 |
| 6. WWR (L-form) | 33.8 |
| 7. WWWR (L-form) | 42.2 |
| 8. WFWRR (L-form) | 39.1 |

TABLE 6

| Sample | LDL-adsorbing ratio (%) |
|---|---|
| 1. WR | 27.7 |
| 2. WAR | 32.3 |
| 3. WAAR | 36.3 |
| 4. WAAAR | 39.3 |
| 5. WAAAAR | 26.3 |
| 6. WAAAAAR | 23.7 |

TABLE 7

| Sample | LDL-binding ratio (%) |
|---|---|
| Example 7 | |
| 1. WFWRK-CONH$_2$ | 71.6 |
| 2. KRWFW-CONH$_2$ | 64.8 |
| Comparative Example 4 | |
| 1. QDGSDEVYK-CONH$_2$ | 10.5 |
| 2. QGDDSEVYK-CONH$_2$ | 1.5 |

TABLE 8

| Sample | LDL-adsorbing ratio (%) |
|---|---|
| Example 8 | |
| 1. WFWRK-CONH$_2$-immobilized Sepharose | 68.5 |
| 2. KRWFW-CONH$_2$-immobilized Sepharose | 68.3 |
| Comparative Example 5 | 6.4 |
| 1. QDGSDEVYK-CONH$_2$-immobilized Sepharose | |

TABLE 9

| Sample | Amount of bradykinin produced (pg/ml) |
|---|---|
| Example 9 | |
| 1. WFWRK-CONH$_2$-immobilized Sepharose | 6,430 |
| 2. KRWFW-CONH$_2$-immobilized Sepharose | 7,790 |
| Comparative Example 6 | 16,600 |
| 1. Commercially available dextran sulfate- | |

TABLE 9-continued

| Sample | Amount of bradykinin produced (pg/ml) |
|---|---|
| immobilized cellulose | |
| Control | |
| 1. No gel (polycarbonate Erlenmeyer flask only) | 8,700 |
| 2. No gel (glass Erlenmeyer flask only) | 20,400 |

TABLE 10

| Sample | Electric charge of the ligand | Results of the visual observation |
|---|---|---|
| Example 10 | | |
| 1. WFWRK-immobilized Sepharose | +2 | Almost no adhesion of blood cells occurred. |
| 2. KRWFW-immobilized Sepharose | +2 | Almost no adhesion of blood cells occurred. |
| Comparative Example 7 | | |
| 1. Polylysine-immobilized Sepharose | more than +100 | Adhesion of erythrocytes occurred. |
| 2. VVWRLTRKRGLKVVV-immobilized Sepharose | +5 | Blood coagulation occurred. |

TABLE 11

| Sample | Affinity to LDL (RU) |
|---|---|
| Example 11 | |
| 1. RRWFW-CONH$_2$ | 16,000 |
| 2. WFWRK-CONH$_2$ | 4,400 |
| 3. KRWFW-CONH$_2$ | 10,500 |
| 4. WFWRR-CONH$_2$ | 2,800 |
| 5. WLFFR-CONH$_2$ | 8,700 |
| 6. FFFRW-CONH$_2$ | 7,800 |
| 7. RFFLW-CONH$_2$ | 5,000 |
| 8. RRWFF-CONH$_2$ | 8,500 |
| 9. RRWAW-CONH$_2$ | 3,400 |
| 10. RKVWW-CONH$_2$ | 2,300 |
| 11. KRVWW-CONH$_2$ | 2,700 |
| 12. KFFLW-CONH$_2$ | 4,600 |
| 13. KMLFF-CONH$_2$ | 3,000 |
| 14. KWLFW-CONH$_2$ | 4,600 |
| 15. RRWWW-CONH$_2$ | 6,600 |
| 16. RRWWF-CONH$_2$ | 13,500 |
| 17. RRFWW-CONH$_2$ | 7,700 |
| 18. RRFFW-CONH$_2$ | 6,200 |
| 19. RRFWF-CONH$_2$ | 9,800 |
| 20. RRWLW-CONH$_2$ | 9,100 |
| 21. RRWVW-CONH$_2$ | 3,500 |
| 22. RRWIW-CONH$_2$ | 5,500 |
| 23. RRWYW-CONH$_2$ | 4,000 |
| 24. RRWSW-CONH$_2$ | 3,200 |
| 25. RRWRW-CONH$_2$ | 3,900 |
| 26. RRWEW-CONH$_2$ | 3,500 |
| Comparative Example 8 | |
| 1. DPSVY-CONH$_2$ | 310 |
| 2. YVSPD-CONH$_2$ | 440 |
| 3. VEEME-CONH$_2$ | 880 |
| 4. EMEEV-CONH$_2$ | 730 |

TABLE 12

| Sample | Affinity to LDL (RU) |
|---|---|
| Example 12 | |
| 1. RRWFW-CONH$_2$ | 2,200 |
| 2. KRWFW-CONH$_2$ | 2,900 |
| 3. WLFFR-CONH$_2$ | 3,900 |
| 4. RRWFF-CONH$_2$ | 2,000 |
| 5. FFFRW-CONH$_2$ | 1,100 |
| 6. RFFLW-CONH$_2$ | 1,800 |
| 7. KFFLW-CONH$_2$ | 1,300 |
| 8. KWLFW-CONH$_2$ | 1,500 |
| 9. KRVWW-CONH$_2$ | 1,300 |
| 10. RRWAW-CONH$_2$ | 5,100 |
| 11. WFWRR-CONH$_2$ | 3,100 |
| 12. RFFW-CONH$_2$ | 4,000 |
| 13. RRFFF-CONH$_2$ | 2,300 |
| 14. FFFRR-CONH$_2$ | 5,700 |
| 15. KRFFF-CONH$_2$ | 1,800 |
| 16. RRWWW-CONH$_2$ | 1,800 |
| 17. RRWWF-CONH$_2$ | 4,800 |
| 18. RRFWW-CONH$_2$ | 4,400 |
| 19. RRFFW-CONH$_2$ | 3,500 |
| 20. RRFWF-CONH$_2$ | 7,800 |
| 21. RRWLW-CONH$_2$ | 8,100 |
| 22. RRWVW-CONH$_2$ | 1,900 |
| 23. RRWIW-CONH$_2$ | 3,500 |
| 24. RRWYW-CONH$_2$ | 2,900 |
| 25. RRWSW-CONH$_2$ | 2,500 |
| 26. RRWRW-CONH$_2$ | 4,500 |
| 27. RRWEW-CONH$_2$ | 4,900 |
| Comparative Example 9 | |
| 1. DPSVY-CONH$_2$ | 250 |
| 2. YVSPD-CONH$_2$ | 210 |
| 3. VEEME-CONH$_2$ | 290 |
| 4. EMEEV-CONH$_2$ | 270 |

TABLE 13

| Sample | LDL-adsorbing ratio (%) |
|---|---|
| Example 13 | |
| 1. RRWFW-CONH$_2$-immobilized Sepharose | 65.2 |
| 2. RRWAW-CONH$_2$-immobilized Sepharose | 63.9 |
| 3. RRWEW-CONH$_2$-immobilized Sepharose | 64.3 |
| 4. RRWRW-CONH$_2$-immobilized Sepharose | 53.2 |
| Comparative Example 10 | 3.1 |
| 1. QDGSDEVYK-CONH$_2$-immobilized Sepharose | |

INDUSTRIAL APPLICABILITY

The peptide of the present invention is advantageous in that the peptide not only has an excellent ability to specifically bind thereto an LDL, but also is free from difficult problems, such as the production of a bradykinin, the activation of blood cells, the adsorption of blood cells onto the peptide and the activation of a blood coagulation system, thus leading to a safety in use of the peptide. Therefore, the peptide of the present invention can be advantageously used not only as a reagent for adsorption-removing an LDL from a body fluid, such as whole blood and plasma, but also as a peptide drug or a carrier peptide for a drug for treating a disease caused by an LDL. Further, the peptide of the present invention which has the ability to bind thereto an LDL has only 10 amino acid residues or less and, hence, is advantageous not only in that it can be easily prepared at low cost, but also in that it has excellent stability, such as sterilization stability and storage stability. Further, when an adsorbent comprising a water-insoluble carrier having bonded thereto the peptide of the present invention is employed in a blood purification treatment device or the like (which is necessarily used for removing the LDL from the blood of a patient suffering from a disease in which, due to a morbid factor, the LDL concentration of the blood is caused to increase to a level higher than that of the LDL concentration of the blood of a healthy person), the LDL can be efficiently, safely removed to advantage on the patient. In addition, when a soft gel (such as an agarose gel) or a hard gel (such as cross-linked polyvinyl alcohol) is used as the above-mentioned water-insoluble carrier in the adsorbent, the adsorbent can be advantageously used as a gel in liquid chromatography and the like for separating from an LDL-containing liquid the LDL in high purity form.

What is claimed is:

1. An absorbent for removing a low density lipoprotein from a body fluid, comprising a water-insoluble carrier having bonded thereto a peptide, said peptide having an amino acid sequence represented by the formula (I) or (II):

$$(X^1)_p\text{-}(\alpha)_m\text{-}(X^2)_q\text{-}(\beta)_n\text{-}(X^3)_r, \text{ or} \tag{I}$$

$$(X^1)_p\text{-}(\beta)_n\text{-}(X^2)_q\text{-}(\alpha)_m\text{-}(X^3)_r \tag{II}$$

wherein the left and right ends of each of formulae (I) and (II) are, respectively, the N- and C-termini; each $\alpha$ is independently Phe or Trp; each $\beta$ is independently Arg or Lys; each $x^1$, each $x^2$ and each $x^3$ are individually, independently an arbitrary amino acid residue; m and n ara, respectively, the numbers of amino acid residues $\alpha$ and $\beta$; and p, q and r are, respectively, the numbers of amino acid residues $x^1$, $x^2$ and $x^3$, wherein p, q and r are the same or different; and wherein m, n, p, q and r satisfy the following requirement:

$$2 \leq m+n+p+q+r \leq 10,$$

wherein m and n satisfy the following requirements:

$$2 \leq m+n \leq 10 \text{ and}$$

$1 \leq m, n \leq 9$, and p, q and r satisfy the following requirements:

$$0 \leq p+q+r \leq 8,$$

$0 \leq p, r \leq 8$ and
$0 \leq q \leq 5$, said peptide having an electric charge (E) satisfying the following requirement:

$$+1 \leq E \leq +4$$

wherein E is defined by the formula:

E=(the number of positive functional groups present in said peptide)–(the number of negative functional groups present in said peptide).

2. The adsorbent according to claim 1, wherein said peptide is directly bonded to said water-insoluble carrier.

3. The adsorbent according to claim 1, wherein said peptide is bonded to said water-insoluble carrier through a spacer material.

4. A method for removing a low density lipoprotein from a body fluid, comprising contacting the body fluid with a peptide having an amino acid sequence represented by the formula (I) or (II):

$$(X^1)_p\text{-}(\alpha)_m\text{-}(X^2)_q\text{-}(\beta)_n\text{-}(X^3)_r, \text{ or} \tag{I}$$

$$(X^1)_p\text{-}(\beta)_n\text{-}(X^2)_q\text{-}(\alpha)_m\text{-}(X^3)_r \tag{II}$$

wherein the left and right ends of each of formulae (I) and (II) are, respectively, the N- and C-termini; each $\alpha$ is independently Phe or Trp; each $\beta$ is independently Arg or Lys; each $x^1$, each $x^2$ and each $x^3$ are individually, independently an arbitrary amino acid residue; m and n ara, respectively, the numbers of amino acid residues $\alpha$ and $\beta$; and P, q and r are, respectively, the numbers of amino acid residues $x^1$, $x^2$ and $x^3$, wherein p, q and r are the same or different; and wherein m, n, p, q and r satisfy the following requirement:

$$2 \leq m+n+p+q+r \leq 10,$$

wherein m and n satisfy the following requirements:

$$2 \leq m+n \leq 10 \text{ and}$$

$1 \leq m, n \leq 9$, and p, q and r satisfy the following requirements:

$$0 \leq p+q+r \leq 8,$$

$0 \leq p, r \leq 8$ and
$0 \leq q \leq 5$, said peptide having an electric charge (E) satisfying the following requirement:

$$+1 \leq E \leq +4$$

wherein E is defined by the formula:

E=(the number of positive functional groups present in said peptide)–(the number of negative functional groups present in said peptide).

* * * * *